(12) United States Patent
Fuchs et al.

(10) Patent No.: US 8,859,110 B2
(45) Date of Patent: Oct. 14, 2014

(54) CYCLIC PHOSPHAZENE COMPOUNDS AND USE THEREOF IN ORGANIC LIGHT EMITTING DIODES

(75) Inventors: Evelyn Fuchs, Mannheim (DE); Oliver Molt, Weinheim (DE); Nicolle Langer, Heppenheim (DE); Christian Lennartz, Schifferstadt (DE); Peter Strohriegl, Bayreuth (DE); Pamela Schroegel, Bayreuth (DE); Herbert Friedrich Boerner, Aachen (DE); Volker Van Elsbergen, Aachen (DE); Arvid Hunze, Kleinblittersdorf (DE); Ralf Krause, Erlangen (DE); Guenter Schmid, Hemhofen (DE)

(73) Assignees: BASF SE, Ludwigshafen (DE); Koninklijke Philips Electronics N.V., Ba Eindhoven (NL); Osram Opto Semiconductors GmbH, Regensburg (DE); Siemens Aktiengesellschaft, Munich (DE)

( * ) Notice: Subject to any disclaimer, the term of this patent is extended or adjusted under 35 U.S.C. 154(b) by 793 days.

(21) Appl. No.: 13/000,261

(22) PCT Filed: Jun. 17, 2009

(86) PCT No.: PCT/EP2009/057505
§ 371 (c)(1),
(2), (4) Date: Mar. 30, 2011

(87) PCT Pub. No.: WO2009/153276
PCT Pub. Date: Dec. 23, 2009

(65) Prior Publication Data
US 2011/0172423 A1    Jul. 14, 2011

(30) Foreign Application Priority Data
Jun. 20, 2008  (EP) ..................... 08158669

(51) Int. Cl.
*H01L 51/50* (2006.01)
*C07F 9/6593* (2006.01)
*H01L 51/00* (2006.01)

(52) U.S. Cl.
CPC ........... *H01L 51/005* (2013.01); *H01L 51/0081* (2013.01); *H01L 51/0072* (2013.01);
(Continued)

(58) Field of Classification Search
None
See application file for complete search history.

(56) References Cited

U.S. PATENT DOCUMENTS 3,138,638 A    6/1964  Bezman et al.
3,917,826 A *  11/1975 Adolphi et al. ............... 514/110
(Continued)

FOREIGN PATENT DOCUMENTS

CH    493 563    7/1970
DE    1 171 916  6/1964
(Continued)

OTHER PUBLICATIONS

Translation for JP 2002-371195 (publication date Dec. 2002).*
(Continued)

*Primary Examiner* — Dawn L. Garrett
(74) *Attorney, Agent, or Firm* — Oblon, Spivak, McClelland, Maier & Neustadt, L.L.P.

(57) ABSTRACT

An organic light-emitting diode comprising at least one cyclic phosphazene compound, a light-emitting layer formed from at least one matrix material and at least one emitter material, wherein the at least one matrix material comprises at least one cyclic phosphazene compound, the use of cyclic phosphazene compounds in organic light-emitting diodes and a device selected from the group consisting of stationary visual display units, mobile visual display units and illumination units comprising at least one inventive organic light-emitting diode, and selected cyclic phosphazene compounds and processes for preparing them.

16 Claims, 2 Drawing Sheets

(52) U.S. Cl.
................ *H01L 51/0074* (2013.01); *H01L 51/5016* (2013.01); *C07F 9/65815* (2013.01); *H01L 51/0085* (2013.01); *H01L 2251/305* (2013.01); *Y10S 428/917* (2013.01)
USPC .......... 428/690; 428/917; 313/504; 313/506; 544/243; 546/15; 546/21; 546/23; 548/414; 549/7; 558/386; 564/13

(56) References Cited

U.S. PATENT DOCUMENTS

| | | |
|---|---|---|
| 2001/0015432 A1 | 8/2001 | Igarashi |
| 2001/0019782 A1 | 9/2001 | Igarashi et al. |
| 2002/0024293 A1 | 2/2002 | Igarashi et al. |
| 2002/0048689 A1 | 4/2002 | Igarashi et al. |
| 2002/0055014 A1 | 5/2002 | Okada et al. |
| 2002/0094453 A1 | 7/2002 | Takiguchi et al. |
| 2006/0255332 A1 | 11/2006 | Becker et al. |
| 2006/0258063 A1 | 11/2006 | Forbes |
| 2007/0108891 A1 | 5/2007 | Watanabe |
| 2007/0196690 A1 | 8/2007 | Ikemizu et al. |

FOREIGN PATENT DOCUMENTS

| | | |
|---|---|---|
| DE | 103 30 761 | 2/2005 |
| EP | 1 191 612 | 3/2002 |
| EP | 1 191 613 | 3/2002 |
| EP | 1 211 257 | 6/2002 |
| JP | 08283416 | 10/1996 |
| JP | 2002 265614 | 9/2002 |
| JP | 2002-265614 A * | 9/2002 |
| JP | 2002-371195 A * | 12/2002 |
| JP | 2006 120762 | 5/2006 |
| JP | 2006 120905 | 5/2006 |
| JP | 2006 278549 | 10/2006 |
| JP | 2007 45742 | 2/2007 |
| JP | 2007 51243 | 3/2007 |
| JP | 2007 59688 | 3/2007 |
| JP | 2007 84635 | 4/2007 |
| JP | 2007 123392 | 5/2007 |
| WO | 00 70655 | 11/2000 |
| WO | 01 41512 | 6/2001 |
| WO | 02 02714 | 1/2002 |
| WO | 02 15645 | 2/2002 |
| WO | 02 060910 | 8/2002 |
| WO | 2005 019373 | 3/2005 |
| WO | 2005 097941 | 10/2005 |
| WO | 2005 097942 | 10/2005 |
| WO | 2005 097943 | 10/2005 |
| WO | 2005 113704 | 12/2005 |
| WO | 2005 123873 | 12/2005 |
| WO | 2006 046980 | 5/2006 |
| WO | 2006 056418 | 6/2006 |
| WO | 2006 067074 | 6/2006 |
| WO | 2006 106842 | 10/2006 |
| WO | 2006 115301 | 11/2006 |
| WO | 2006 121811 | 11/2006 |
| WO | 2006 126389 | 11/2006 |
| WO | 2007 018067 | 2/2007 |
| WO | 2007 023659 | 3/2007 |
| WO | 2007 029461 | 3/2007 |
| WO | 2007 052431 | 5/2007 |
| WO | 2007 058080 | 5/2007 |
| WO | 2007 058104 | 5/2007 |
| WO | 2007 058255 | 5/2007 |
| WO | 2007 060826 | 5/2007 |
| WO | 2007 069539 | 6/2007 |
| WO | 2007 069542 | 6/2007 |
| WO | 2007 095118 | 8/2007 |
| WO | 2007 115790 | 10/2007 |
| WO | 2007 115970 | 10/2007 |
| WO | 2007 115981 | 10/2007 |
| WO | 2008 000726 | 1/2008 |
| WO | 2008 000727 | 1/2008 |
| WO | 2008 122603 | 10/2008 |

OTHER PUBLICATIONS

Translation for JP 2002-265614 (publication date Sep. 2002).*
U.S. Appl. No. 13/516,117, filed Aug. 27, 2012, Molt, et al.
Bolink, et al., "Efficient Blue Emitting Organic Light Emitting Diodes Based on Fluorescent Solution Processable Cyclic Phosphazenes", Organic Electronics, vol. 9, No. 2, pp. 155-163, XP 022489968, ISSN: 1566-1199, (Oct. 25, 2007).
Bolink, H. J. et al., "Solution Processable Phosphorescent Dendrimers Based on Cyclic Phosphazenes for Use in Organic Light Emitting Diodes (OLEDs)" Chem. Commun., pp. 618-620, XP 002542457, (Dec. 4, 2007).
Baldo, A. M. et al., "Very High-Efficiency Green Organic Light-Emitting Devices Based on Electrophosphorescence", Applied Physics Letter. vol. 75, No. 1, pp. 4-6 (Jul. 5, 1999).
Vicente, V. et al., "Synthesis and Structural Studies ($^1$H, $^{13}$C, $^{31}$P NMR and X-ray) of New C-Bonded Cyclotriphosphazenes With Heterocyclic Substituents From Novel Phosphinic Acid Derivatives", New. J. Chem., vol. 28, pp. 418-424, (Feb. 13, 2004).
Vicente, V. et al., "Determination of $^{31}$P, $^{31}$P Coupling Constants in Cyclotriphosphazenes and Their Influence on $^1$H and $^{13}$C NMR Spectra of Phosphorus Substituents", Magnetic Resonance in Chemistry, vol. 41, pp. 183-192, (2003).
Combes-Chamalet, C. et al., "Synthesis and X-ray Structural Studies of New Spiro-Cyclotri-Phosphazenes", J. Chem. Soc., Perkin Trans. 2, pp. 15-18, (1997).
Appel, R. et al., "Eine Neue Synthese Von Organyl-Substituierten Triazatri-Phosphor(V)inen (Cyclotriphosphazenen) Und Tetrazatetra-Phosph(V)Ocinen (Cyclotetraphosphazenen)$^1$", Chem. Ber., vol. 106, pp. 3455-3460, (1973).
International Search Report issued Sep. 9, 2009 in PCT/EP09/057505 filed Jun. 17, 2009.

* cited by examiner

CYCLIC PHOSPHAZENE COMPOUNDS AND USE THEREOF IN ORGANIC LIGHT EMITTING DIODES

BACKGROUND OF THE INVENTION

1. Field of the Invention

The present invention relates to an organic light-emitting diode comprising at least one cyclic phosphazene compound, a light-emitting layer formed from at least one matrix material and at least one emitter material, wherein the at least one matrix material comprises at least one cyclic phosphazene compound, to the use of cyclic phosphazene compounds in organic light-emitting diodes, and to a device selected from the group consisting of stationary visual display units, mobile visual display units and illumination units comprising at least one inventive organic light-emitting diode, and to selected cyclic phosphazene compounds and processes for preparing them.

2. Description of the Background

Organic light-emitting diodes (OLEDs) exploit the propensity of materials to emit light when they are excited by electrical current. OLEDs are of particular interest as an alternative to cathode ray tubes and to liquid-crystal displays for producing flat visual display units. Owing to the very compact design and the intrinsically low power consumption, devices comprising OLEDs are suitable especially for mobile applications, for example for applications in cellphones, laptops, etc., and for illumination.

The basic principles of the way in which OLEDs work and suitable structures (layers) of OLEDs are specified, for example, in WO 2005/113704 and the literature cited therein.

The light-emitting materials (emitters) used may, as well as fluorescent materials (fluorescence emitters), be phosphorescent materials (phosphorescence emitters). The phosphorescence emitters are typically organometallic complexes which, in contrast to the fluorescence emitters which exhibit singlet emission, exhibit triplet emission (M. A. Baldo et al., Appl. Phys. Lett. 1999, 75, 4-6). For quantum-mechanical reasons, when the phosphorescence emitters are used, up to four times the quantum efficiency, energy efficiency and power efficiency is possible.

Of particular interest are organic light-emitting diodes with long operative lifetime, good efficiency, high stability to thermal stress and a low use voltage and operating voltage, and which especially emit light in the blue region of the electromagnetic spectrum.

In order to implement the aforementioned properties in practice, it is not just necessary to provide suitable emitter materials, but the other components of the OLED (complementary materials) must also be matched to one another in suitable device compositions. Such device compositions may comprise, for example, specific matrix materials in which the actual light emitter is present in distributed form. In addition, the compositions may comprise blocker materials, in which case hole blockers, exciton blockers and/or electron blockers may be present in the device compositions. Additionally or alternatively, the device compositions may additionally comprise hole injection materials and/or electron injection materials and/or charge transport materials such as hole conductor materials and/or electron conductor materials. The selection of the aforementioned materials which are used in combination with the actual light emitter has a significant influence on properties including the efficiency and the lifetime of the OLEDs.

The prior art proposes numerous different materials for use in the different layers of OLEDs.

DE 103 30 761 A1 relates to mixtures of organic semiconductors and matrix materials capable of emission, to the use thereof and to electronic components which comprise them. The mixtures according to DE 103 30 761 are formed from at least two substances, one of which serves as a matrix material and the other is an emission material capable of emission. The matrix material is a compound which comprises at least one structural unit of the L=X and/or M=X form, where the X radical has at least one non-bonding electron pair, the L radical is P, As, Sb or Bi, the M radical is S, Se, Te, and can if appropriate also form glasslike layers. DE 103 30 761 A1 specifies numerous different suitable matrix materials which are covered by one of the aforementioned formulae. The matrix material may, among other materials, be a cyclic phosphazene, where the cyclic phosphazene may have from 4 to 14 ring atoms and may be substituted by numerous different substituents on the phosphorus. Specific examples of phosphazenes suitable as matrix materials are not specified in DE 103 30 761 A1, since DE 103 30 761 A1 preferentially specifies specific spiro compounds (not phosphazenes) as matrix materials.

JP 08-283416 specifies cyclic phosphazene compounds and organic thin-film elements which comprise them. These are specific cyclic phosphazenes which have 6 or 8 ring members, and in which the phosphorus atom is substituted by phenoxy groups or N,N'-diphenyl-N-(3-methylphenyl)-1,1'-biphenyl-4,4'-diamino]-3-phenyloxy groups, where at least two of the radicals on the phosphorus are phenoxy groups. According to JP 08-283416, the specific phosphazenes are notable in that they have a high thermal stability and a high amorphous stability, and are free of chlorine residues and other impurities. The specific cyclic phosphazenes are, according to JP 08-283416 A, used in hole transport and hole injection layers.

JP 2006-278549 A relates to an organic light-emitting diode which has a layer which comprises a (cyclo)phosphazene compound. Suitable (cyclo)phosphazene compounds specified in JP 2006-278549 A are (cyclo)phosphazene compounds which have from 4 to 8 ring members. Suitable substituents on the phosphorus are —OR$^1$ and —OR$^2$ groups joined via oxygen, a 6-membered phosphazene with —O—C$_6$H$_4$—CF$_3$ and/or —O—C$_6$H$_4$—F substituents being specified explicitly.

V. Vicente et al. (New. J. Chem., 2004, 28, 418-424) disclose the syntheses and structures of cyclotriphosphazenes with heterocyclic substituents bonded via carbon atoms. The heterocyclic substituents used are 2-thienyl, 3-thienyl and 3,3'-bithienyl-2,2'-ylene groups. On the basis of the geometric properties of the cyclotriphosphazenes specified, it is suspected that they can form stacked structures with possibly interesting electronic properties through coordination of the free heteroatoms to transition metals. No specific possible uses of the cyclotriphosphazenes are mentioned in V. Vicente et al.

V. Vicente et al. Magn. Res. Chem. 2003, 41:183-192 disclose NMR studies of cyclotriphosphazenes. Among others, structures of cyclotriphosphazenes with heterocyclic substituents bonded via carbon atoms are studied by NMR spectroscopy. In addition to the cyclotriphosphazenes substituted by 2-thienyl, 3-thienyl and 3,3'-bithienyl-2,2'-ylene groups disclosed in the aforementioned document, cyclotriphosphazenes which bear 2-pyridyl groups are disclosed, as are cyclotriphosphazenes which bear spiro groups. The NMR studies are intended to serve to elucidate electronic properties of the cyclotriphosphazenes studied. No specific possible uses of the cyclotriphosphazenes are mentioned in V. Vicente et al.

C. Combes-Chamalet et al. J. Chem. Soc., Perkin Trans. 2, 1997 15-18 relates to the synthesis and structure of spirocyclotriphosphazenes. These might—like cyclotriphosphazenes—be of interest for the formation of inclusion adducts with water or organic solvents. No specific possible uses of the spiro-cyclotriphosphazenes are mentioned in C. Combes-Chamalet et al.

It is an object of the present invention, with respect to the prior art cited above, to provide materials suitable for use in OLEDs, especially for use as matrix materials in a light-emitting layer, and/or for use as hole blocker materials, said light-emitting layer preferably comprising at least one blue emitter. More particularly, complementary materials for OLEDs (preferably matrix materials, charge transport materials, blocker materials, charge injection materials) shall thus be provided, said materials having a high triplet energy, in order that light emission of the blue emitter used in the OLEDs is ensured. Furthermore, the materials shall be suitable for providing OLEDs which ensure good efficiencies, good operative lifetimes and a high stability to thermal stress, and a low use voltage and operating voltage of the OLEDs.

SUMMARY OF THE INVENTION

This object is achieved by an organic light-emitting diode comprising at least one cyclic phosphazene compound of the general formula (I)

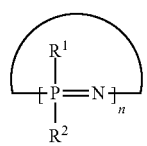

(I)

in which:
n is from 3 to 8, preferably 3 or 4, more preferably 3;
$R^1$, $R^2$
 are each independently substituted or unsubstituted aryl, substituted or unsubstituted heteroaryl, substituted or unsubstituted alkyl, substituted or unsubstituted aryloxy, substituted or unsubstituted alkyloxy, unsubstituted or substituted cycloalkyl, unsubstituted or substituted heterocycloalkyl, unsubstituted or substituted alkenyl, unsubstituted or substituted alkynyl, unsubstituted or substituted aralkyl or halogen, preferably each independently substituted or unsubstituted aryl, substituted or unsubstituted heteroaryl, substituted or unsubstituted alkyl, substituted or unsubstituted aryloxy, substituted or unsubstituted alkyloxy, more preferably each independently substituted or unsubstituted aryl, substituted or unsubstituted heteroaryl or substituted or unsubstituted aryloxy, most preferably each independently substituted or unsubstituted aryl or substituted or unsubstituted heteroaryl, where $R^1$ and $R^2$ in the n groups may each be the same or different;
or
 the aforementioned $R^1$ and $R^2$ radicals are each independently, in the n groups of the general formula (I), joined to one another via a bond, a $C_1$-$C_6$-alkylene bridge, preferably a $C_1$-$C_2$-alkylene bridge, an arylene bridge, preferably a 1,2-phenylene bridge, or a $C_2$-$C_6$-alkenylene bridge, preferably a $C_2$-$C_4$-alkenylene bridge, such that the $R^1$ and $R^2$ radicals together with the phosphorus atom to which they are joined form a cycle; $R^1$ and $R^2$ preferably form—in the case where they are joined to one another—together independently, in the n groups of the general formula (I), one of the following groups:

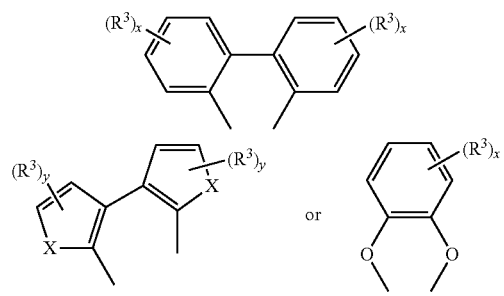

in which:
$R^3$ are each independently substituted or unsubstituted aryl, substituted or unsubstituted heteroaryl, substituted or unsubstituted alkyl, substituted or unsubstituted aryloxy, substituted or unsubstituted alkyloxy, unsubstituted or substituted cycloalkyl, unsubstituted or substituted heterocycloalkyl, unsubstituted or substituted alkenyl, unsubstituted or substituted alkynyl, unsubstituted or substituted aralkyl or halogen, preferably F, or pseudohalogen, preferably CN, preferably each independently substituted or unsubstituted aryl, substituted or unsubstituted heteroaryl, substituted or unsubstituted alkyl, substituted or unsubstituted aryloxy, substituted or unsubstituted alkyloxy or F or CN;
x are each independently 0, 1, 2, 3 or 4, preferably 0, 1 or 2;
y are each independently 0, 1 or 2, preferably 0 or 1.

In the present invention, at least one of the $R^1$ and $R^2$ radicals present in the n groups is joined to at least one of the phosphorus atoms of the cyclic phosphazenes of the formula (I) not via an oxygen atom, the at least one $R^1$ or $R^2$ radical preferably being bonded via a carbon atom.

DETAILED DESCRIPTION OF THE INVENTION

Figure 1:
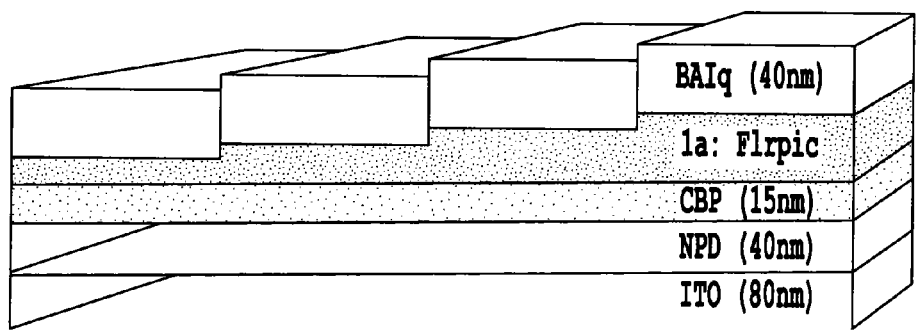
FIG. 1 shows a layer sequence for a diode.

The cyclic phosphazene compounds used in the inventive OLED are notable for outstanding suitability for use in OLEDs. More particularly, the cyclic phosphazene compounds used in accordance with the invention, in which at least one of the $R^1$ and $R^2$ radicals is joined to at least one of the phosphorus atoms not via an oxygen atom and preferably via a carbon atom, compared to corresponding cyclic phosphazenes whose substituents are joined to the phosphorus atoms exclusively via oxygen atoms, are notable in that they generally have high glass transition temperatures and, in thin layers as used in OLEDs, have higher amorphousness. This achieves optimal performance of OLEDs which comprise at least one compound of the formula (I). In addition, the cyclic phosphazene compounds used in accordance with the invention preferably have an energy difference between the electronically excited triplet state $T_1$ and the base state $S_0$ which is sufficiently great that they are useful as complementary materials, especially matrix materials, blocker materials, charge transport materials and/or charge injection materials for blue emitters.

Depending on their substitution pattern and the electronic properties of the layers used in the OLED, the cyclic phosphazene compounds used in accordance with the invention may, in addition to use as matrix materials in the light-emitting layer and use as hole/exciton blocker materials, also be used as electron conductors, electron injection materials and/or electron/exciton blocker materials, hole Injection materials and/or hole conductors. Corresponding layers of OLEDs are known in principle to those skilled in the art and are specified, for example, in WO 2005/113704 or WO 2005/019373.

Preference is given to using the cyclic phosphazene compounds used in accordance with the invention as matrix material in the light-emitting layer and/or as hole/exciton blocker material and/or electron conductors, more preferably as matrix material in the light-emitting layer and/or hole/exciton blockers.

In the context of the present application, the terms unsubstituted or substituted aryl radical or group, unsubstituted or substituted heteroaryl radical or group, unsubstituted or substituted alkyl radical or group, unsubstituted or substituted cycloalkyl radical or group, unsubstituted or substituted heterocycloalkyl radical or group, unsubstituted or substituted alkenyl radical or group, unsubstituted or substituted alkynyl radical or group, unsubstituted or substituted aralkyl radical or group, and groups with donor and/or acceptor action are each defined as follows:

An aryl radical (or group) is understood to mean a radical which has a base skeleton of from 6 to 30 carbon atoms, preferably from 6 to 18 carbon atoms, and which is formed from an aromatic ring or a plurality of fused aromatic rings. Suitable base skeletons are, for example, phenyl, naphthyl, anthracenyl or phenanthrenyl. This base skeleton may be unsubstituted (i.e. all carbon atoms which are substitutable bear hydrogen atoms) or be substituted at one, more than one or all substitutable positions of the base skeleton. Suitable substituents are, for example, deuterium, alkoxy radicals, aryloxy radicals, alkylamino groups, arylamino groups, carbazolyl groups, silyl groups, alkyl radicals, preferably alkyl radicals having from 1 to 8 carbon atoms, more preferably methyl, ethyl or i-propyl, aryl radicals, preferably $C_6$-aryl radicals, which may in turn be substituted or unsubstituted, heteroaryl radicals, preferably heteroaryl radicals which comprise at least one nitrogen atom, more preferably pyridyl radicals, alkenyl radicals, preferably alkenyl radicals which bear one double bond, more preferably alkenyl radicals with one double bond and from 1 to 8 carbon atoms, or groups with donor or acceptor action. Suitable groups with donor or acceptor action are specified below. Most preferably, the substituted aryl radicals bear substituents selected from the group consisting of methyl, ethyl, isopropyl, alkoxy, heteroaryl, CN and aryloxy. The aryl radical or the aryl group is preferably a $C_6$-$C_{18}$-aryl radical, more preferably a $C_6$-aryl radical, which is optionally substituted by at least one or more than one of the aforementioned substituents. More preferably, the $C_6$-$C_{18}$-aryl radical, preferably $C_6$-aryl radical, has none, one, two, three or four, most preferably none, one or two, of the aforementioned substituents. In one embodiment, particularly preferred aryl radicals suitable as $R^1$ and $R^2$ radicals are $C_6$-aryl radicals which have one or two substituents.

A heteroaryl radical or a heteroaryl group is understood to mean radicals which differ from the aforementioned aryl radicals in that, in the base skeleton of the aryl radicals, at least one carbon atom is replaced by a heteroatom, and in that the base skeleton of the heteroaryl radicals has preferably from 5 to 18 ring atoms. Preferred heteroatoms are N, O and S. Particularly preferred heteroaryl radicals suitable as $R^1$ and $R^2$ radicals are nitrogen-containing heteroaryl radicals. Most preferably, one or two carbon atoms of the base skeleton are replaced by heteroatoms, preferably nitrogen. Especially preferably, the base skeleton is selected from systems such as pyridine, pyrimidine and five-membered heteroaromatics such as pyrrole, furan, pyrazole, imidazole, thiophene, oxazole, thiazole, triazole. In addition, the heteroaryl radicals may be fused ring systems, for example carbazolyl radicals or azacarbazolyl radicals. The base skeleton may be substituted at one, more than one or all substitutable positions of the base skeleton. Suitable substituents are the same as have already been specified for the aryl groups.

An alkyl radical or an alkyl group is understood to mean a radical having from 1 to 20 carbon atoms, preferably from 1 to 10 carbon atoms, more preferably from 1 to 8 and most preferably from 1 to 4 carbon atoms. This alkyl radical may be branched or unbranched and may optionally be interrupted by one or more heteroatoms, preferably Si, N, O or S, more preferably N, O or S. In addition, this alkyl radical may be substituted by one or more of the substituents specified for the aryl groups. It is likewise possible that the alkyl radical bears one or more (hetero)aryl groups. In the context of the present application, for example, benzyl radicals are thus substituted alkyl radicals. All of the above-listed (hetero)aryl groups are suitable. The alkyl radicals are more preferably selected from the group consisting of methyl, ethyl, isopropyl, n-propyl, n-butyl, isobutyl and tert-butyl; very particular preference is given to methyl and ethyl.

A cycloalkyl radical or a cycloalkyl group is understood to mean a radical having from 3 to 20 carbon atoms, preferably from 3 to 10 carbon atoms, more preferably from 3 to 8 carbon atoms. This base skeleton may be unsubstituted (i.e. all carbon atoms which are substitutable bear hydrogen atoms) or may be substituted at one, more than one or all substitutable positions of the base skeleton. Suitable substituents are the groups already specified above for the aryl radicals. Examples of suitable cycloalkyl radicals are cyclopropyl, cyclopentyl and cyclohexyl.

A heterocycloalkyl radical or a heterocycloalkyl group is understood to mean radicals which differ from the aforementioned cycloalkyl radicals in that, in the base skeleton of the cycloalkyl radicals, at least one carbon atom is replaced by a heteroatom. Preferred heteroatoms are N, O and S. Most preferably, one or two carbon atoms of the base skeleton of the cycloalkyl radicals are replaced by heteroatoms. Examples of suitable heterocycloalkyl radicals are radicals derived from pyrrolidine, piperidine, piperazine, tetrahydrofuran, dioxane.

An alkenyl radical or an alkenyl group is understood to mean a radical which corresponds to the aforementioned alkyl radicals having at least two carbon atoms, with the difference that at least one C—C single bond of the alkyl radical is replaced by a C—C double bond. The alkenyl radical preferably has one or two double bonds.

An alkynyl radical or an alkynyl group is understood to mean a radical which corresponds to the aforementioned alkyl radicals having at least two carbon atoms, with the difference that at least one C—C single bond of the alkyl radical is replaced by a C—C triple bond. The alkynyl radical preferably has one or two triple bonds.

A $C_1$-$C_6$-alkylene bridge, preferably a $C_1$-$C_2$-alkylene bridge, is understood to mean an alkylene group having from 1 to 6, preferably 1 or 2, carbon atoms in the main chain. The alkylene bridge may be substituted by one or more of the substituents mentioned for the aryl groups. It is likewise possible that the alkylene radical bears one or more (hetero) aryl groups. In addition, one or more heteroatoms, preferably —O— or —NR'— where R' is an alkyl, aryl, heteroaryl, cycloalkyl or heterocycloalkyl radical may be present in the main chain of the alkylene bridge.

A $C_2$-$C_6$-alkenylene bridge, preferably a $C_2$-$C_4$-alkenylene bridge, is understood to mean an alkenylene group having from 2 to 6, preferably from 2 to 4, carbon atoms in the main chain. The alkenylene bridge may be substituted by one or more of the substituents mentioned for the aryl groups. It is likewise possible that the alkenylene radical bears one or more (hetero)aryl groups. In addition, one or more heteroatoms, preferably —O— or —NR'—where R' is an alkyl, aryl, heteroaryl, cycloalkyl or heterocycloalkyl radical may be present in the main chain of the alkenylene bridge.

An arylene bridge is understood to mean an arylene group which has preferably from 6 to 18 carbon atoms in the base skeleton. The arylene group may be formed from one aromatic ring or a plurality of fused aromatic rings. Suitable base skeletons are, for example, phenylene, naphthylene, anthracenylene or phenanthrenylene. The arylene bridge may optionally be substituted by one or more of the substituents mentioned for the aryl groups. The arylene bridge is preferably a phenylene bridge, which is more preferably unsubstituted. The phenylene bridge is most preferably a 1,2-phenylene bridge.

Halogen groups are understood to mean preferably F, Cl and Br, more preferably F and Cl, most preferably F.

Pseudohalogen groups are understood to mean preferably CN, SCN and OCN, more preferably CN.

In the context of the present application, a group or a substituent with donor or acceptor action is understood to mean the following groups:

groups with donor action are understood to mean groups which have a +I and/or +M effect, and groups with acceptor action to mean groups which have a −I and/or −M effect. Suitable groups with donor or acceptor action are halogen radicals, preferably F, Cl, Br, alkoxy radicals or aryloxy radicals, $OR^2$, carbonyl radicals, ester radicals, both oxycarbonyl and carbonyloxy, amino groups, $NR^2$, amide radicals, $CH_2F$ groups, $CHF_2$ groups, $CF_3$ groups, CN groups, thio groups, sulfonic acid groups, sulfonic ester groups, boronic acid groups, boronic ester groups, phosphonic acid groups, phosphonic ester groups, phosphine radicals, sulfoxide radicals, sulfonyl radicals, sulfide radicals, $SR^2$, nitro groups, OCN, borane radicals, silyl groups, stannate radicals, imino groups, hydrazine radicals, hydrazone radicals, oxime radicals, nitroso groups, diazo groups, phosphine oxide groups, hydroxyl groups or SCN groups. Very particular preference is given to F, CN, aryloxy, alkoxy, amino, $CF_3$ groups, sulfonyl, silyl, sulfide and heteroaryl. Very especially preferred are heteroaryl, silyl, alkoxy or aryloxy, amino and CN.

The aforementioned groups with donor or acceptor action do not rule out the possibility that further radicals and substituents which are specified in the present application and are not listed in the above list of groups with donor or acceptor action have donor or acceptor action.

The aryl radicals or groups, heteroaryl radicals or groups, alkyl radicals or groups, cycloalkyl radicals or groups, heterocycloalkyl radicals or groups, alkenyl radicals or groups, alkynyl radicals or groups and groups with donor and/or acceptor action, and also the alkylene and arylene radicals or groups, may—as mentioned above—be substituted or unsubstituted. In the context of the present application, an unsubstituted group is understood to mean a group in which the substitutable atoms of the group bear hydrogen atoms. In the context of the present application, a substituted group is understood to mean a group in which one or more substitutable atom(s) bear a substituent instead of a hydrogen atom at least in one position. Suitable substituents are the substituents specified above for the aryl radicals or groups.

When radicals with the same numbering occur more than once in the compounds according to the present application, these radicals may each independently be defined as specified.

The at least one $R^1$ or $R^2$ radical which is present in the n groups of the cyclic phosphazene compounds of the general formula (I) and is joined to at least one of the phosphorus atoms of the cyclic phosphazene compounds not via an oxygen atom and is preferably joined via a carbon atom is more preferably an unsubstituted or substituted aryl radical or an unsubstituted or substituted heteroaryl radical. Suitable aryl radicals and heteroaryl radicals and suitable substituents have been mentioned above. Very particular preference is given to $C_6$-aryl radicals, for example unsubstituted $C_6$-aryl radicals or $C_6$-aryl radicals substituted by one or two alkyl or alkoxy groups. The at least one $R^1$ or $R^2$ radical may, for example, be phenyl, 3,5-dimethylphenyl or 4-methoxyphenyl. Particularly preferred heteroaryl radicals are heteroaryl radicals which have from 5 to 18 ring atoms, most preferably from 5 to 13 ring atoms and may be substituted or unsubstituted. Very particular preference is given to nitrogen-containing heteroaryl radicals. In principle, the nitrogen-containing heteroaryl radicals in the cyclic phosphazene compounds of the general formula (I) used in accordance with the invention may be joined to at least one of the phosphorus atoms of the cyclic phosphazene compounds via a nitrogen atom or a carbon atom. The nitrogen-containing heteroaryl radicals are preferably joined to the phosphorus atom via a carbon atom. Examples of suitable heteroaryl radicals are 3-pyridyl, 4-pyridyl, azacarbazolyl or 3-carbazolyl.

In addition, the $R^1$ and $R^2$ radicals in one or more of the n groups of the cyclic phosphazene compounds of the general formula (I) may each independently be joined to one another via a bond, a $C_1$-$C_6$-alkylene bridge, preferably a $C_1$-$C_2$-alkylene bridge, an arylene bridge, preferably a 1,2-phenylene bridge, or a $C_2$-$C_6$-alkenylene bridge, preferably a $C_2$-$C_4$-alkenylene bridge, such that the $R^1$ and $R^2$ radicals together with the phosphorus atom to which they are joined form a cycle; $R^1$ and $R^2$ preferably form—in the case where they are joined to one another—together independently, in the n groups of the general formula (I), one of the following groups:

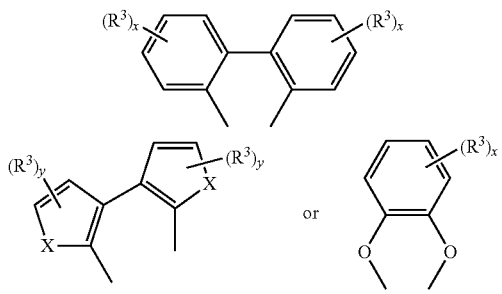

in which:
$R^3$ are each independently substituted or unsubstituted aryl, substituted or unsubstituted heteroaryl, substituted or unsubstituted alkyl, substituted or unsubstituted aryloxy, substituted or unsubstituted alkyloxy, unsubstituted or substituted cycloalkyl, unsubstituted or substituted heterocycloalkyl, unsubstituted or substituted alkenyl, unsubstituted or substituted alkynyl, unsubstituted or substituted aralkyl or halogen, preferably F, or pseudohalogen, preferably CN, preferably each independently substituted or unsubstituted aryl, substituted or unsubstituted heteroaryl, substituted or unsubstituted alkyl, substituted or unsubstituted aryloxy, substituted or unsubstituted alkyloxy or F or CN;

x are each independently 0, 1, 2, 3 or 4, preferably 0, 1 or 2;

y are each independently 0, 1 or 2, preferably 0 or 1.

Very particular preference is given to those cyclic phosphazene compounds of the general formula (I) in which:

$R^1$, $R^2$
are each independently substituted or unsubstituted aryl or substituted or unsubstituted heteroaryl, where $R^1$ and $R^2$ in the n groups may each be the same or different.

Preferably, $R^1$ and $R^2$ in the n groups are each identical. Suitable substituted or unsubstituted aryl radicals and suitable substituted or unsubstituted heteroaryl radicals have been specified above. Particularly suitable substituted or unsubstituted aryl radicals and particularly suitable substituted or unsubstituted heteroaryl radicals are the radicals specified for the at least one $R^1$ or $R^2$ radical which is present in the n groups and is joined to at least one of the phosphorus atoms of the cyclic phosphazene compounds not via an oxygen atom and preferably via a carbon atom. This means that, in a very particularly preferred embodiment, all $R^1$ and $R^2$ radicals of the cyclic phosphazene compounds of the formula (I) are joined to the particular phosphorus atoms not via an oxygen atom, but preferably via a nitrogen atom or carbon atom and more preferably via a carbon atom.

In a further preferred embodiment, n in the cyclic phosphazenes of the general formula (I) is 3 or 4, more preferably 3. This means that cyclic phosphazene compounds of the formula (I) which have 6 or 8 ring members are particularly preferred, very particular preference being given to cyclic phosphazene compounds of the formula (I) which have 6 ring members (cyclotriphosphazenes).

Very particular preference is further given to cyclic phosphazene compounds of the formula (I) in which n is 3 and the at least one $R^1$ or $R^2$ radical which is present in the n groups and is bonded to at least one of the phosphorus atoms not via an oxygen atom and preferably via a carbon atom is a substituted or unsubstituted aryl radical or a substituted or unsubstituted heteroaryl radical.

The cyclic phosphazene compounds used in accordance with the invention thus most preferably have the formula (Ia)

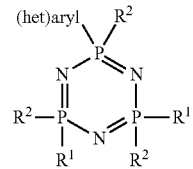
(Ia)

in which (het)aryl is unsubstituted or substituted $C_{6-14}$-aryl, e.g. phenyl, $C_1$-$C_6$-alkylphenyl, $C_1$-$C_6$-dialkylphenyl, $C_1$-$C_6$-alkoxyphenyl or $C_1$-$C_6$-dialkoxyphenyl, or unsubstituted or substituted heteroaryl which has from 5 to 14 ring atoms and is joined to the P of the phosphazene ring via a carbon atom, e.g. unsubstituted or substituted carbazolyl, unsubstituted or substituted azacarbazolyl or unsubstituted or substituted pyridyl;

$R^1$, $R^2$ are each independently substituted or unsubstituted aryl, substituted or unsubstituted heteroaryl, substituted or unsubstituted alkyl, substituted or unsubstituted aryloxy, substituted or unsubstituted alkyloxy, where $R^1$ and independently substituted or unsubstituted aryl or substituted or unsubstituted heteroaryl, where $R^1$ and $R^2$ may each be the same or different and are more preferably unsubstituted or substituted $C_{6-14}$-aryl, e.g. phenyl, $C_1$-$C_6$-alkylphenyl, $C_1$-$C_6$-dialkylphenyl, $C_1$-$C_6$-alkoxyphenyl or $C_1$-$C_6$-dialkoxyphenyl or unsubstituted or substituted heteroaryl which has from 5 to 14 ring atoms, e.g. unsubstituted or substituted pyridyl, unsubstituted or substituted carbazolyl, unsubstituted or substituted azacarbazolyl, where $R^1$ and $R^2$ may each be the same or different;

or the aforementioned $R^1$ and $R^2$ radicals are each independently joined to one another via a bond, a $C_1$-$C_6$-alkylene bridge, preferably a $C_1$-$C_2$-alkylene bridge, an arylene bridge, preferably a 1,2-phenylene bridge, or a $C_2$-$C_6$-alkenylene bridge, preferably a $C_2$-$C_4$-alkenylene bridge, such that the $R^1$ and $R^2$ radicals together with the phosphorus atom to which they are joined form a cycle; $R^1$ and $R^2$ preferably form—in the case where they are joined to one another—together independently, in the n groups of the general formula (I), one of the following groups:

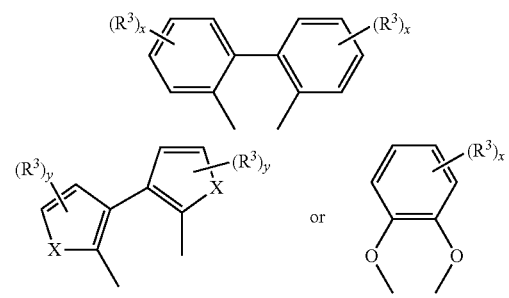

in which:

$R^3$ are each independently substituted or unsubstituted aryl, substituted or unsubstituted heteroaryl, substituted or unsubstituted alkyl, substituted or unsubstituted aryloxy, substituted or unsubstituted alkyloxy, unsubstituted or substituted cycloalkyl, unsubstituted or substituted heterocycloalkyl, unsubstituted or substituted alkenyl, unsubstituted or substituted alkynyl, unsubstituted or substituted aralkyl or halogen, preferably F, or pseudohalogen, preferably CN, preferably each independently substituted or unsubstituted aryl, substituted or unsubstituted heteroaryl, substituted or unsubstituted alkyl, substituted or unsubstituted aryloxy, substituted or unsubstituted alkyloxy or F or CN;

x are each independently 0, 1, 2, 3 or 4, preferably 0, 1 or 2;

y are each independently 0, 1 or 2, preferably 0 or 1.

Very particularly preferred embodiments of (het)aryl and of $R^1$ and $R^2$ are the radicals specified above for $R^1$ and $R^2$.

Most preferably, the $R^1$ and $R^2$ radicals and the (het)aryl radical in the cyclic phosphazene compounds of the formula (Ia) are identical, i.e. very particular preference is given to cyclic phosphazene compounds of the general formula (Iaa):

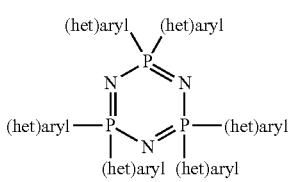
(Iaa)

in which (het)aryl is unsubstituted or substituted $C_{6-14}$-aryl, e.g. phenyl, $C_1$-$C_6$-alkylphenyl, $C_1$-$C_6$-dialkylphenyl, $C_1$-$C_6$-alkoxyphenyl or $C_1$-$C_6$-dialkoxyphenyl or unsubstituted or substituted heteroaryl which has from 5 to 14 ring atoms and is bonded to the P of the phosphazene ring via a carbon atom, e.g. unsubstituted or substituted carbazolyl, unsubstituted or substituted azacarbazolyl or unsubstituted or substituted pyridyl.

(Het)aryl is preferably unsubstituted or substituted $C_6$-aryl or unsubstituted or substituted nitrogen-containing $C_6$-heteroaryl or substituted or unsubstituted carbazolyl or substituted or unsubstituted azacarbazolyl. Suitable substituents have been specified above. Preferred substituents are $C_1$- to $C_6$-alkyl, e.g. methyl, ethyl, n-propyl, isopropyl, n-butyl, isobutyl, sec-butyl, tert-butyl, CN and $C_1$- to $C_6$-alkoxy, e.g. methoxy, ethoxy. Examples of suitable (het)aryl radicals are phenyl, $C_1$-$C_6$-alkylphenyl such as methylphenyl, $C_1$-$C_6$-dialkylphenyl such as dimethylphenyl, $C_1$-$C_6$-alkoxyphenyl such as methoxyphenyl, $C_1$-$C_6$-dialkoxyphenyl such as dimethoxyphenyl, pyridyl, $C_1$-$C_6$-alkylpyridyl such as methylpyridyl, carbazolyl, $C_1$-$C_6$-alkylcarbazolyl such as methylcarbazolyl, N—$C_1$-$C_6$-alkylcarbazolyl such as N-methylcarbazolyl, $C_1$-$C_6$-dialkylcarbazolyl such as dimethylcarbazolyl, azacarbazolyl and N—$C_1$-$C_6$-azacarbazolyl such as N-methylazacarbazolyl.

Examples of particularly suitable cyclic phosphazene compounds of the formula (Iaa) are the phosphazene compounds of the formulae Iaaa to Iaar specified below:

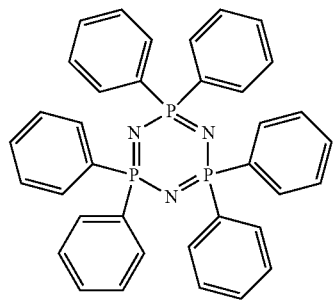
(Iaaa)

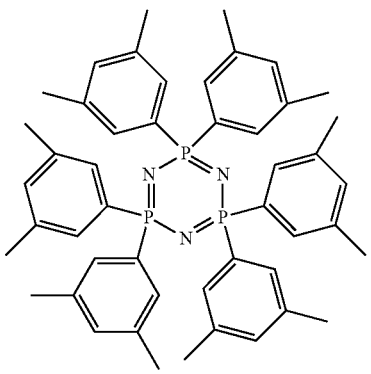
(Iaab)

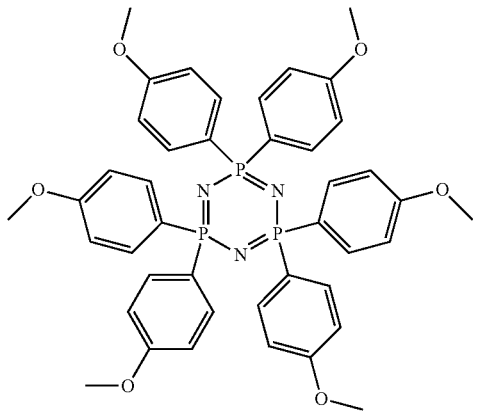
(Iaac)

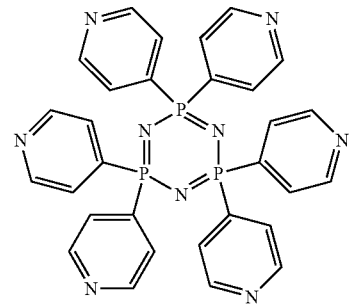
(Iaad)

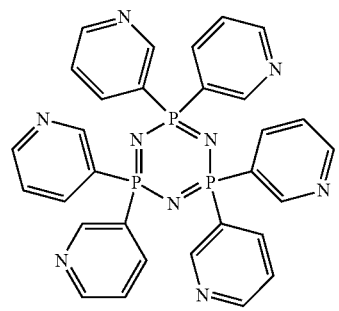
(Iaae)

(Iaaf)
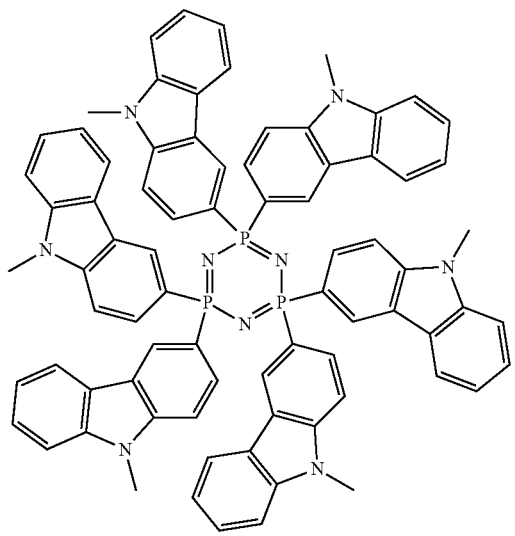
(Iaag)
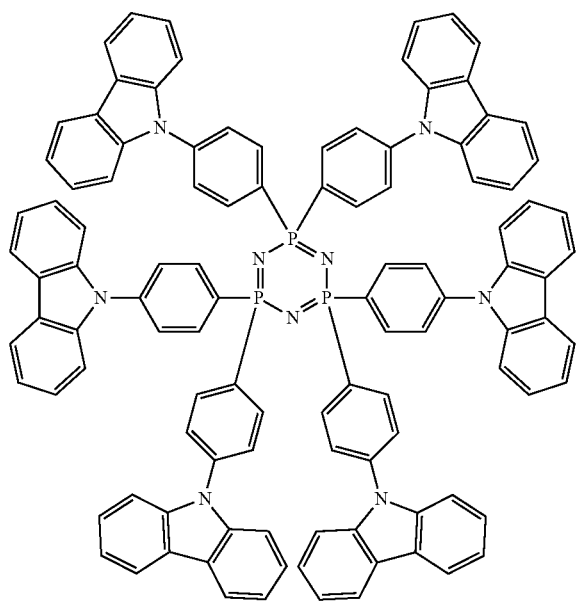
(Iaah)
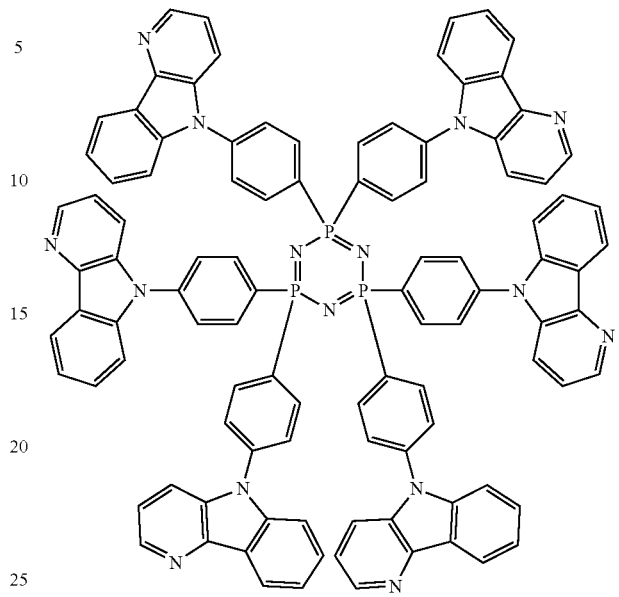
(Iaai)
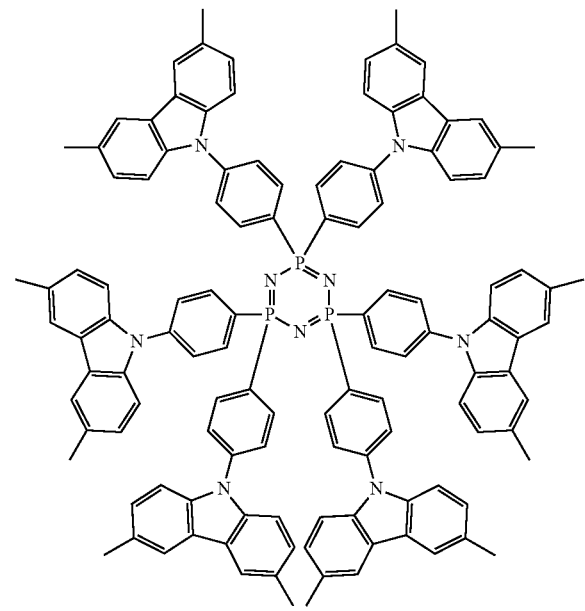

-continued
(Iaaj)
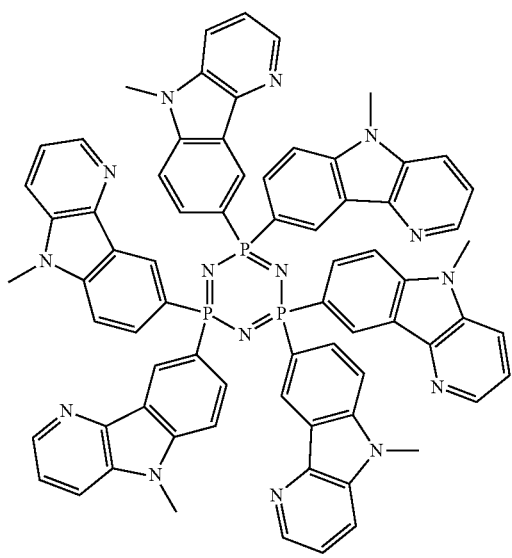
(Iaak)
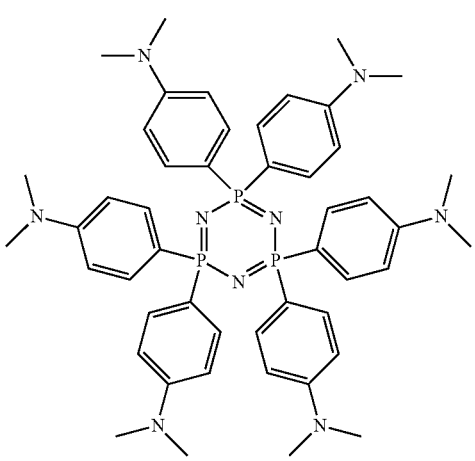
(Iaal)
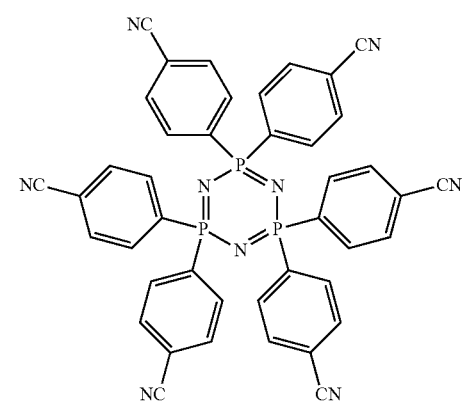
(Iaam)
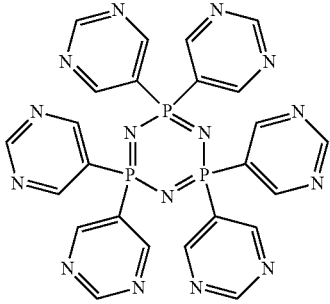
(Iaan)
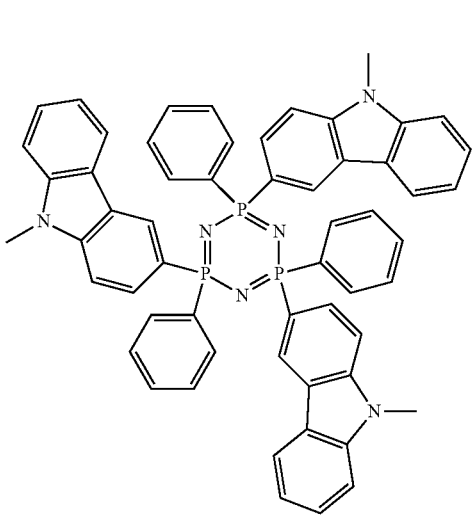
(Iaao)
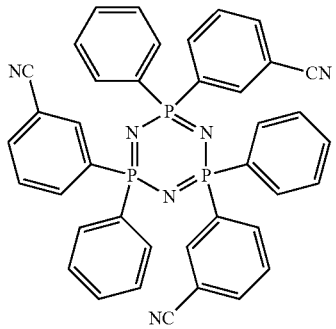
(Iaap)
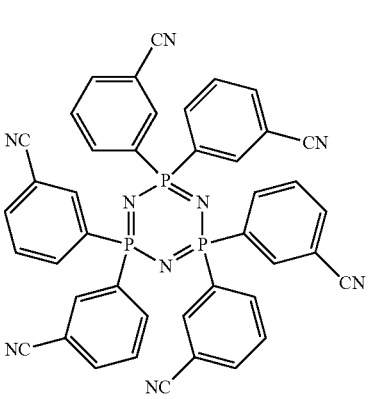

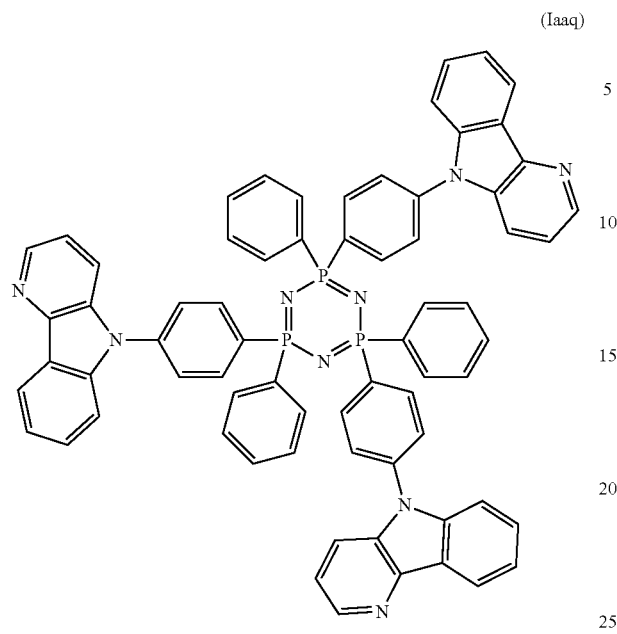
(Iaaq)

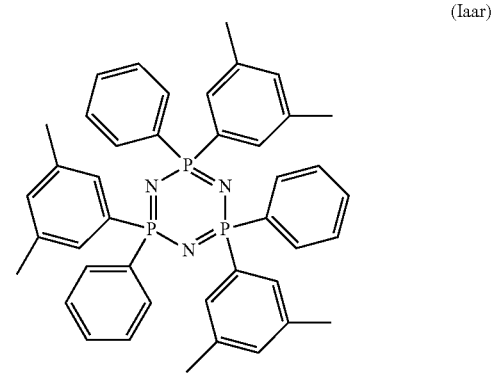
(Iaar)

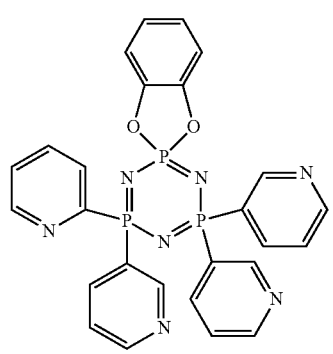
(Iaas)

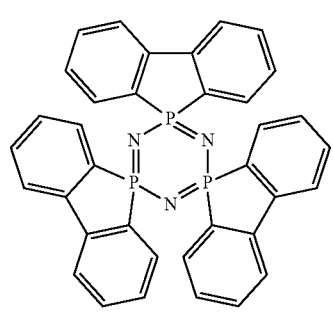
(Iaat)

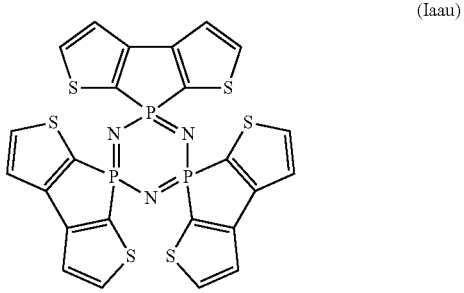 [SMILES: c1cc2c(s1)P1(=NP3(=NP4(=N1)c1sccc1-c1ccsc14)c1sccc1-c1ccsc13)c1sccc1-2]
(Iaau)

It has been found that especially the aforementioned cyclic phosphazene compounds of the general formula (Ia), especially the compounds in which $R^1$ and $R^2$ have the same definitions as (het)aryl, i.e. in which all radicals on the phosphazene base skeleton are aromatic or heteroaromatic radicals which are bonded to the particular phosphorus atom via a carbon atom—in addition to high glass transition temperatures and good amorphousness—themselves are characterized by an energy difference between the electronically excited triplet state $T_1$ and the base state $S_0$ of at least 2.8 eV. This makes these cyclic phosphazene compounds of the general formula (Ia) useful especially as matrix materials, blocker materials, charge transport materials and/or charge injection materials, preferably matrix materials and/or blocker materials such as hole blocker materials, for blue phosphorescence emitters. The cyclic phosphazene compounds of the formula (I) are thus usable as: hole injection, hole conduction, hole blocker, electron injection, electron conduction, electron blocker, exciton blocker and/or matrix materials. Preference is given to using the cyclic phosphazene compounds of the formula (I) as matrix materials and/or hole blocker materials.

In addition to the aforementioned electronic properties, it is additionally essential that the cyclic phosphazene compounds used as materials for OLEDs have glass transition temperatures which enable use of the cyclic phosphazene compounds in OLEDs. The cyclic phosphazene compounds used in accordance with the invention have glass transition temperatures $T_g$ of generally at least 50° C., preferably at least 65° C.

Cyclic phosphazene compounds of the formula (I) in which n is 3 (cyclotriphosphazenes) and which have at least one substituted nitrogen-containing heteroaryl radical, at least one substituted aryl radical, at least one substituted or unsubstituted carbazolyl radical or at least one substituted or unsubstituted azacarbazolyl radical which is joined to at least one of the phosphorus atoms via a carbon atom are not known in the prior art.

The present invention therefore further provides cyclic phosphazene compounds of the general formula (II)

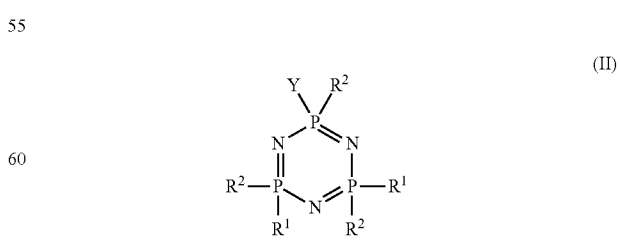
(II)

in which
Y is substituted $C_{6-14}$-aryl, substituted nitrogen-containing heteroaryl which has from 5 to 14 ring atoms and is joined to the phosphorus atom of the phosphazene ring via a carbon atom, substituted or unsubstituted carbazolyl which is joined to the phosphorus atom of the phosphazene ring via a carbon atom, or substituted or unsubstituted azacarbazolyl which is joined to the phosphorus atom of the phosphazene ring via a carbon atom;

$R^1$, $R^2$ are each independently substituted or unsubstituted aryl, substituted or unsubstituted heteroaryl, substituted or unsubstituted alkyl, substituted or unsubstituted aryloxy, substituted or unsubstituted alkyloxy, F, where $R^1$ and $R^2$ may each be the same or different and are preferably each independently substituted or unsubstituted aryl, substituted or unsubstituted alkyl, substituted or unsubstituted aryloxy or substituted or unsubstituted heteroaryl, more preferably each independently substituted or unsubstituted aryl or substituted or unsubstituted heteroaryl, where $R^1$ and $R^2$ may each be the same or different; more preferably unsubstituted or substituted $C_{6-14}$-aryl or unsubstituted or substituted heteroaryl which has from 5 to 14 ring atoms, where $R^1$ and $R^2$ may each be the same or different.

Preferred $R^1$ and $R^2$ radicals correspond to the preferred $R^1$ and $R^2$ radicals specified for the cyclic phosphazene compounds of the formula (I), though $R^1$ and $R^2$ are not joined via a bridge. Preferred nitrogen-containing heteroaryl radicals and preferred substituted aryl radicals likewise correspond to the radicals specified for the cyclic phosphazene compounds of the formula (I).

As in the cyclic phosphazene compounds of the formula (I) and of the formulae (Ia) and (Iaa), it is also preferred in the cyclic phosphazene compounds of the formula (II) that all $R^1$, $R^2$ and Y radicals in the cyclic phosphazene compounds of the formula (II) are defined identically. Very particularly preferred cyclic phosphazene compounds of the formula (II) are cyclic phosphazene compounds of the formula (IIa)

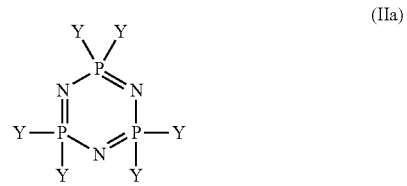

(IIa)

in which

Y is substituted $C_{6-14}$-aryl, substituted nitrogen-containing heteroaryl which has from 5 to 14 ring atoms and is joined to the phosphorus atom of the phosphazene ring via a carbon atom, substituted or unsubstituted carbazolyl which is joined to the phosphorus atom of the phosphazene ring via a carbon atom, or substituted or unsubstituted azacarbazolyl which is joined to the phosphorus atom of the phosphazene ring via a carbon atom.

Y is preferably substituted $C_6$-aryl or substituted nitrogen-containing heteroaryl having 6 ring atoms, substituted or unsubstituted carbazolyl or substituted or unsubstituted azacarbazolyl. Suitable substituents have been specified above. Preferred substituents are $C_1$- to $C_6$-alkyl, e.g. methyl, ethyl, n-propyl, isopropyl, n-butyl, isobutyl, sec-butyl, tert-butyl, CN and $C_1$- to $C_6$-alkoxy, e.g. methoxy, ethoxy. Examples of suitable Y radicals are $C_1$-$C_6$-alkylphenyl such as methylphenyl, $C_1$-$C_6$-dialkylphenyl such as dimethylphenyl, $C_1$-$C_6$-alkoxyphenyl such as methoxyphenyl, $C_1$-$C_6$-dialkoxyphenyl such as dimethoxyphenyl, $C_1$-$C_6$-alkylpyridyl such as methylpyridyl, carbazolyl, $C_1$-$C_6$-alkylcarbazolyl such as methylcarbazolyl, N—$C_1$-$C_6$-alkylcarbazolyl such as N-methylcarbazolyl, $C_1$-$C_6$-dialkylcarbazolyl such as dimethylcarbazolyl, azacarbazolyl and N—$C_1$-$C_6$-azacarbazolyl such as N-methylazacarbazolyl.

Examples of particularly preferred compounds of the formula (IIa) are the cyclic phosphazene compounds of the formulae (Iaab, Iaac and Iaaf to Iaar).

The cyclic phosphazene compounds of the formula (I) or (II) are preferably prepared by cyclocondensation of corresponding phosphinamides, in accordance with the process for preparing cyclotriphosphazenes and cyclotetraphosphazenes disclosed in R. Appel et al. Chem. Ber. 106, 3455-3460 (1973). The corresponding phosphinamides can be obtained by amidating the particular phosphinic acids. The scheme which follows shows, by way of example, the preparation of cyclic phosphazene compounds of the formula (I) or (II), by way of example using cyclotriphosphazenes (n in the compounds of the formula (I)=3) in which the $R^1$ and $R^2$ radicals on all phosphorus atoms are each defined identically ($R^1$):

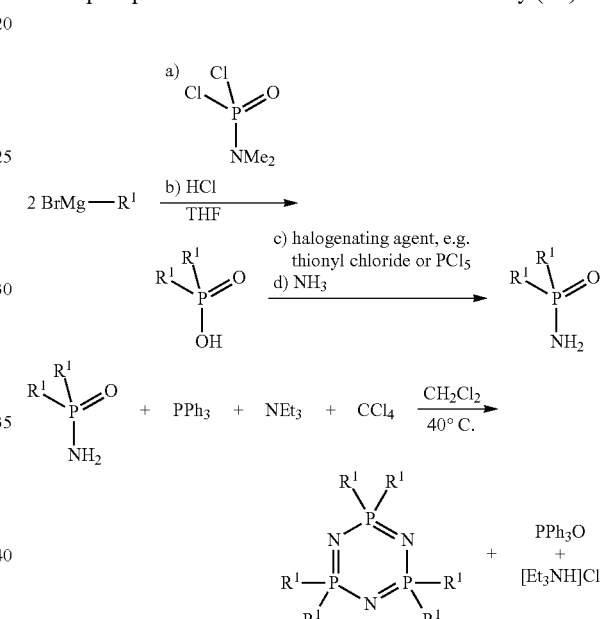

Suitable reaction conditions for preparing the cyclic phosphazene compounds of the formula (I) or (II) correspond to the reaction conditions specified in V. Vicente et al. New J. Chem. 2004, 28, 418-424 for preparing hexa(2-thienyl)cyclotriphosphazenes and hexa(3-thienyl)cyclotriphosphazenes and are additionally specified in the examples section of the present application for the preparation of selected particularly preferred compounds. In addition, suitable reaction conditions for preparing cyclic phosphazenes in which $R^1$ and $R^2$ are joined to one another (spirocyclophosphazenes) are disclosed, for example, in C. Combes-Chamalet et al. J. Chem. Soc., Perkin Trans. 2, 1997, 15-18.

The cyclic phosphazene compounds of the formula (I) used in accordance with the invention and the inventive cyclic phosphazene compounds of the formula (II) may—as mentioned above—be used in different layers of the inventive organic light-emitting diode, suitable layer sequences in OLEDs being known to those skilled in the art and being specified below.

In one embodiment, the present invention relates to organic light-emitting diodes in which the cyclic phosphazene compounds of the formula (I) or (II) are used as a matrix in the light-emitting layer.

In a further embodiment, the present invention relates to an inventive organic light-emitting diode in which the cyclic phosphazene compounds of the formula (I) or (II) are used in the blocking layer for holes as a hole/exciton blocker and/or in the electron injection layer and/or in the electron conductor layer. It is likewise possible that the compounds of the formula (I) or (II) are present in the light-emitting layer and/or one or more of the aforementioned layers.

In a further embodiment, the present invention relates to an inventive organic light-emitting diode in which the cyclic phosphazene compounds of the formula (I) or (II) are used in the blocking layer for electrons as an electron/exciton blocker and/or in the hole injection layer and/or in the hole conductor layer. It is likewise possible that the compounds of the formula (I) or (II) are additionally present in the light-emitting layer and/or one or more of the layers specified below.

Depending on the layer in which the cyclic phosphazene compounds of the formula (I) or (II) are used, they have different preferred $R^1$ and $R^2$ radicals and different n indices. In addition, the properties of the cyclic phosphazene compounds (as matrix material, hole/exciton blocker material or electron/exciton blocker material, hole or electron conductor material and/or hole or electron injection material) are dependent on the electronic properties (relative positions of the HOMOs and LUMOs) of the particular layers used in the inventive OLED. It is thus possible, by virtue of suitable substitution of the cyclic phosphazene compounds of the formula (I) or (II), to adjust the HOMO and LUMO orbital positions to the further layers used in the inventive OLED, and thus to achieve a high stability of the OLED and hence a long operative lifetime and good efficiencies.

The principles regarding the relative positions of HOMO and LUMO in the individual layers of an OLED are known to those skilled in the art. The principles, by way of example with regard to the properties of the blocking layer for electrons and of the blocking layer for holes, in relation to the light-emitting layer are detailed hereinafter:

The LUMO of the blocking layer for electrons is energetically higher than the LUMO of the materials used in the light-emitting layer (both of the emitter material and of any matrix materials used). The greater the energetic difference of the LUMOs of the blocking layer for electrons and of the materials in the light-emitting layer, the better are the electron- and/or exciton-blocking properties of the blocking layer for electrons. Suitable substitution patterns of the cyclic phosphazene compounds of the formula (I) or (II) suitable as electron and/or exciton blocker materials thus depend upon factors including the electronic properties (especially the position of the LUMO) of the materials used in the light-emitting layer.

The HOMO of the blocking layer for holes is energetically lower than the HOMOs of the materials present in the light-emitting layer (both of the emitter materials and of any matrix materials present). The greater the energetic difference of the HOMOs of the blocking layer for holes and of the materials present in the light-emitting layer, the better are the hole- and/or exciton-blocking properties of the blocking layer for holes. Suitable substitution patterns of the cyclic phosphazene compounds of the formula (I) or (II) suitable as hole and/or exciton blocker materials thus depend upon factors including the electronic properties (especially the position of the HOMOs) of the materials present in the light-emitting layer.

Comparable considerations relating to the relative position of the HOMOs and LUMOs of the different layers used in the inventive OLED apply to the further layers which may be used in the OLED and are known to those skilled in the art.

Organic light-emitting diodes (OLEDs) are in principle formed from several layers:
1. anode (1)
2. hole-transporting layer (2)
3. light-emitting layer (3)
4. electron-transporting layer (4)
5. cathode (5)

However, it is also possible that the OLED does not have all of the layers mentioned; for example, an OLED comprising layers (1) (anode), (3) (light-emitting layer) and (5) (cathode) is likewise suitable, in which case the functions of layers (2) (hole-transporting layer) and (4) (electron-transporting layer) are assumed by the adjacent layers. OLEDs which have layers (1), (2), (3) and (5) or layers (1), (3), (4) and (5) are likewise suitable.

The inventive cyclic phosphazene compounds of the formula (I) can be used in one or more different layers of an OLED. The present invention therefore further provides for the use of cyclic phosphazene compounds of the formula (I) or (II) in OLEDs.

The cyclic phosphazene compounds of the formula (I) or (II) are, in a preferred embodiment, used as matrix material in the light-emitting layer. The present invention therefore further provides an organic light-emitting diode comprising a light-emitting layer formed from at least one matrix material and at least one emitter material, in which the at least one matrix material comprises at least one cyclic phosphazene compound of the formula (I) or (II). The present invention further provides a light-emitting layer formed from at least one matrix material and at least one emitter material, in which the at least one matrix material comprises at least one cyclic phosphazene compound of the formula (I) or (II). Preferred cyclic phosphazene compounds of the formula (I) or (II) are specified above.

In general, the proportion of the at least one cyclic phosphazene compound of the formula (I) or (II) in the light-emitting layer of the inventive OLEDs is from 10 to 99% by weight, preferably from 50 to 99% by weight, more preferably from 70 to 97% by weight. The proportion of the at least one emitter material in the light-emitting layer is generally from 1 to 90% by weight, preferably from 1 to 50% by weight, more preferably from 3 to 30% by weight, where the proportions of the at least one cyclic phosphazene compound of the formula (I) or (II) and the at least one emitter material add up to 100% by weight. However, it is also possible that the light-emitting layer, as well as the at least one cyclic phosphazene compound of the general formula (I) or (II) and the at least one emitter material, comprises further substances, for example further matrix material other than the cyclic phosphazene compound of the formula (I) or (II), suitable further matrix materials being known to those skilled in the art.

The individual aforementioned layers of the OLED may in turn be composed of 2 or more layers. For example, the hole-transporting layer may be composed of one layer into which holes are injected from the electrode and one layer which transports the holes away from the hole-injecting layer into the light-emitting layer. The electron-transporting layer may likewise consist of a plurality of layers, for example one layer into which electrons are injected by the electrode and one layer which receives electrons from the electron-injecting layer and transports them into the light-emitting layer. These specified layers are each selected according to factors such as energy level, thermal resistance and charge carrier mobility, and also energy differential of the layers mentioned with the organic layers or the metal electrodes. Those skilled in the art are capable of selecting the structure of the OLEDs in such a way that it is matched optimally to the inventive metal complexes used preferably as emitter substances.

In order to obtain particularly efficient OLEDs, the HOMO (highest occupied molecular orbital) of the hole-transporting layer should be aligned to the work function of the anode, and the LUMO (lowest unoccupied molecular orbital) of the electron-transporting layer aligned to the work function of the cathode.

Suitable materials for the aforementioned layers (anode, cathode, hole and electron injection materials, hole and electron transport materials and hole and electron blocker materials, matrix materials, fluorescence and phosphorescence emitters) are known to those skilled in the art and are specified, for example, in H. Meng, N. Herron, *Organic Small Molecule Materials for Organic Light-Emitting Devices in Organic Light-Emitting Materials and Devices*, eds.: Z. Li, H. Meng, Taylor & Francis, 2007, Chapter 3, pages 295 to 411.

The anode (1) is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals include the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to emit the light formed.

Suitable hole transport materials for the layer (2) of the inventive OLEDs are disclosed, for example, in Kirk-Othmer Encyclopedia of Chemical Technology, 4th Edition, Vol. 18, pages 837 to 860, 1996. Either hole-transporting molecules or polymers may be used as the hole transport material. Customarily used hole-transporting molecules are selected from the group consisting of 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylamino-styrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p(diethylamino)styryl]-5-[(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4',4"-tris(N,N-diphenylamino)triphenylamine (TDTA) and porphyrin compounds, and also phthalocyanines such as copper phthalocyanines. Customarily used hole-transporting polymers are selected from the group consisting of polyvinylcarbazoles, (phenylmethyl)polysilanes, PEDOT (poly(3,4-ethylenedioxythiophene)), preferably PEDOT doped with PSS (polystyrenesulfonate), and polyanilines. It is likewise possible to obtain hole-transporting polymers by doping hole-transporting molecules into polymers such as polystyrene and polycarbonate. Suitable hole-transporting molecules are the molecules already mentioned above.

It is additionally possible to use—in one embodiment—metal complexes, for example carbene complexes, as hole transport materials, in which case the band gap of the at least one hole transport material is generally larger than the band gap of the emitter material used. In the context of the present application, the band gap is understood to mean the triplet energy. Suitable carbene complexes are, for example, carbene complexes as described in WO 2005/019373 A2, WO 2006/056418 A2, WO 2005/113704, WO 2007/115790 and WO 2007/115981, and in prior European applications EP 07 118 677.9 and EP 08 153 303.6, which were yet to be published at the priority date of the present application.

The light-emitting layer (3) comprises at least one emitter material. In a preferred embodiment, the light-emitting layer is formed from at least one matrix material and at least one emitter material, the matrix material preferably being at least one cyclic phosphazene compound of the formula (I) or (II). Preferred cyclic phosphazene compounds have been specified above. Since the cyclic phosphazene compounds of the formula (I) or (II) used in accordance with the invention, in a particularly preferred embodiment, are notable for an energy difference between the electronically excited triplet state $T_1$ and the base state $S_0$ of at least 2.8 eV, the cyclic phosphazene compounds of the formula (I) or (II) used in accordance with the invention are preferably used together with at least one blue emitter as an emitter material. The emission maximum of the emitter material of the light-emitting layer light is more preferably in the range from 400 to 500 nm, most preferably from 430 to 490 nm. The at least one emitter material may in principle be a fluorescence or phosphorescence emitter, suitable emitter materials being known to those skilled in the art. The at least one emitter material is preferably a phosphorescence emitter, most preferably a phosphorescence emitter which emits blue light. The phosphorescence emitter compounds used with preference are based on metal complexes, of which especially the complexes of the metals Ru, Rh, Ir, Pd and Pt, in particular the complexes of Ir, have gained significance. The cyclic phosphazene compounds of the formula (I) or (II) used in accordance with the invention are particularly suitable for use together with such metal complexes.

Suitable metal complexes for use in the inventive OLEDs are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1, WO 2006/056418, WO 2007/115981, WO 2007/115970, WO 2008/000726, WO 2008/000727, WO 2007/018067, US 2007/0108891, WO 2007/058080, WO 2007/058104, WO 2006/106842, WO 2007/058255, WO 2007/069542, JP 2007/084635, JP 2007/045742, JP 2006/120762, JP 2006/120905, JP 2007/051243, JP 2007/059688, JP 2007/123392, JP 2007/051243, US 2007/0196690, WO 2006/126389, WO 2007/023659, WO 2007/029461, WO 2007/052431, WO 2007/060826, WO 2007/069539, WO 2005/123873, WO 2006/046980, WO 2006/121811, WO 2007/095118, WO 2005/097941, WO 2005/097942, WO 2005/097943, and European applications EP 07 118677.9 and EP 08 153303.6, which were yet to be published at the priority date of the present application, and in prior PCT application PCT/EP2008/054087, which was yet to be published at the priority date of the present application.

Further suitable metal complexes are the commercially available metal complexes tris(2-phenylpyridine)iridium (III), iridium(III)tris(2-(4-tolyl)pyridinato-N,$C^{2'}$), iridium (III)tris(1-phenylisoquinoline), iridium(III)bis(2-(2'-benzothienyl))pyridinato-N,C$^{3'}$)(acetylacetonate), iridium(III)bis(2-(4,6-difluorophenyl)pyridinato-N,C$^2$)picolinate, iridium(III)bis(1-phenylisoquinoline)(acetylacetonate), iridium(III)bis(dibenzo[f,h]-quinoxaline)(acetylacetonate), iridium(III)bis(2-methyldibenzo[f,h]quinoxaline)-(acetylacetonate) and tris(3-methyl-1-phenyl-4-trimethyl-acetyl-5-pyrazoline)terbium(III).

Additionally suitable are the following commercially available materials: tris(dibenzoylacetonato)mono(phenanthroline)europium(III), tris(dibenzoylmethane)-mono(phenanthroline)europium(III), tris(dibenzoylmethane)mono(5-aminophenan-throline)europium(III), tris(di-2-naphthoylmethane)mono(phenanthroline)europium(III), tris(4-bromobenzoylmethane)mono(phenanthroline)europium(III), tris(di(biphenyl-methane))mono(phenanthroline)europium(III), tris(dibenzoylmethane)mono(4,7-diphenylphenanthroline)europium(III), tris(dibenzoylmethane)mono(4,7-di-methylphenanthroline)europium(III), tris(dibenzoylmethane)mono(4,7-dimethyl-phenanthrolinedisulfonic acid)europium(III) disodium salt, tris[di(4-(2-(2-ethoxy-ethoxy)ethoxy)benzoylmethane)]mono(phenanthroline)europium(III) and tris[di(4-(2-(2-ethoxyethoxy)ethoxy)benzoylmethane)]mono(5-aminophenanthroline)europium(III).

More preferably, the emitter materials are metal complexes, for example metal complexes disclosed in the aforementioned documents which have an emission maximum in the range from 400 to 500 nm, preferably from 430 to 490 nm.

Further triplet emitters suitable with preference are carbene complexes. In a preferred embodiment of the present invention, the cyclic phosphazene compounds of the formula (I) or (II) are used in the light-emitting layer as a matrix material together with carbene complexes, most preferably together with blue-emitting carbene complexes, as triplet emitters. Suitable carbene complexes are known to those skilled in the art and are specified in some of the aforementioned applications and below.

In a further preferred embodiment, the cyclic phosphazene compounds of the formula (I) or (II) are used as a hole/exciton blocker material together with carbene complexes as a triplet emitter. The cyclic phosphazene compounds of the formula (I) or (II) may additionally be used both as matrix materials and as hole/exciton blocker materials together with carbene complexes as triplet emitters.

Suitable metal complexes for use together with the cyclic phosphazene compounds of the formula (I) or (II) as matrix materials and/or hole/exciton blocker materials and/or charge transport materials and/or charge injection materials, preferably matrix materials and/or hole blocker materials, in OLEDs are thus, for example, also carbene complexes, as described in WO 2005/019373 A2, WO 2006/056418 A2 and WO 2005/113704, WO 2007/115970 and in WO 2007/115981, and in the prior European applications EP 07 118677.9 and EP 08 153303.6, which were yet to be published at the priority date of the present application. Reference is hereby made to the disclosure of the cited WO and EP applications and these disclosures shall be considered to be incorporated by reference into the content of the present application.

Suitable electron transport materials for the layer (4) of the inventive OLEDs include metals chelated with oxinoid compounds, such as tris(8-hydroxyquinolato)aluminum (Alq$_3$), compounds based on phenanthroline such as 2,9-dimethyl-4,7-diphenyl-1,10-phenanthroline (DDPA=BCP) or 4,7-diphenyl-1,10-phenanthroline (DPA) and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). The layer (4) may serve both to ease the electron transport and as a buffer layer or as a barrier layer in order to prevent quenching of the exciton at the interfaces of the layers of the OLED. The layer (4) preferably improves the mobility of the electrons and reduces quenching of the exciton.

Of the materials specified above as hole transport materials and electron-transporting materials, some can fulfill a plurality of functions. For example, some of the electron-conducting materials are simultaneously hole-blocking materials when they have a low-lying HOMO.

The charge transport layers may also be electronically doped in order to improve the transport properties of the materials used, in order firstly to make the layer thicknesses more generous (avoidance of pinholes/short circuits) and secondly to minimize the operating voltage of the device. For example, the hole transport materials may be doped with electron acceptors; for example, phthalocyanines or arylamines such as TPD or TDTA may be doped with tetrafluorotetracyanoquinodimethane (F4-TCNQ). The electron transport materials may, for example, be doped with alkali metals, for example Alq$_3$ with lithium. Electronic doping is known to those skilled in the art and is disclosed, for example, in W. Gao, A. Kahn, J. Appl. Phys., Vol. 94, No. 1, Jul. 1, 2003 (p-doped organic layers); A. G. Werner, F. Li, K. Harada, M. Pfeiffer, T. Fritz, K. Leo, Appl. Phys. Lett., Vol. 82, No. 25, Jun. 23, 2003 and Pfeiffer et al., Organic Electronics 2003, 4, 89-103.

The cathode (5) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used. In addition, lithium-comprising organometallic compounds or LiF may be applied between the organic layer and the cathode in order to reduce the operating voltage.

The OLED of the present invention may additionally comprise further layers which are known to those skilled in the art. For example, a layer which eases the transport of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to ease the transport of the negative charge and/or to match the band gaps between the layers to one another. Alternatively, this layer may serve as a protective layer.

In a preferred embodiment, the inventive OLED, in addition to the layers (1) to (5), comprises at least one of the further layers mentioned below:
a hole injection layer between the anode (1) and the hole-transporting layer (2);
a blocking layer for electrons and/or excitons between the hole-transporting layer (2) and the light-emitting layer (3);
a blocking layer for holes and/or excitons between the light-emitting layer (3) and the electron-transporting layer (4);
an electron injection layer between the electron-transporting layer (4) and the cathode (5).

As already mentioned above, it is, however, also possible that the OLED does not have all of the layers (1) to (5) mentioned; for example, an OLED having the layers (1) (anode), (3) (light-emitting layer) and (5) (cathode) is likewise suitable, in which case the functions of the layers (2) (hole-transporting layer) and (4) (electron-transporting layer) are assumed by the adjacent layers. OLEDs which have the layers (1), (2), (3) and (5) or the layers (1), (3), (4) and (5) are likewise suitable.

Those skilled in the art know how suitable materials have to be selected (for example on the basis of electrochemical investigations). Suitable materials for the individual layers and suitable OLED structures are known to those skilled in the art and disclosed, for example, in WO2005/113704.

Furthermore, each of the specified layers of the inventive OLED may be composed of two or more layers. In addition, it is possible that some or all of the layers (1), (2), (3), (4) and (5) have been surface-treated in order to increase the efficiency of charge carrier transport. The selection of the materials for each of the layers mentioned is preferably determined by obtaining an OLED having a high efficiency.

The inventive OLED can be produced by methods known to those skilled in the art. In general, the OLED is produced by successive vapor deposition of the individual layers onto a suitable substrate. Suitable substrates are, for example, glass or polymer films. For the vapor deposition, customary techniques may be used, such as thermal evaporation, chemical vapor deposition and others. In an alternative process, the organic layers may be coated from solutions or dispersions in suitable solvents, in which case coating techniques known to those skilled in the art are employed. Compositions which, in addition to the at least one inventive metal complex, have a polymeric material in one of the layers of the OLED, preferably in the light-emitting layer, are generally applied as a layer by means of solution-mediated processes.

In general, the different layers have the following thicknesses: anode (1) from 500 to 5000 Å, preferably from 1000 to 2000 Å; hole-transporting layer (2) from 50 to 1000 Å, preferably from 200 to 800 Å; light-emitting layer (3) from 10 to 1000 Å, preferably from 100 to 800 Å; electron-transporting layer (4) from 50 to 1000 Å, preferably from 200 to 800 Å; cathode (5) from 200 to 10 000 Å, preferably from 300 to 5000 Å. The position of the recombination zone of holes and electrons in the inventive OLED and thus the emission spectrum of the OLED may be influenced by the relative thickness of each layer. This means that the thickness of the electron transport layer should preferably be selected such that the electron/hole recombination zone is within the light-emitting layer. The ratio of the layer thicknesses of the individual layers in the OLED is dependent upon the materials used. The layer thicknesses of any additional layers used are known to those skilled in the art.

Use of the cyclic phosphazene compounds of the formula (I) or (II) in at least one layer of the inventive OLED, for example as a matrix material in the light-emitting layer of the inventive OLEDs and/or as a hole/exciton blocker material in the blocking layer for holes and/or excitons or as a charge transport material and/or as a charge injection material and/or as an electron blocker material, allows OLEDs with high efficiency to be obtained. The efficiency of the inventive OLEDs may additionally be improved by optimizing the other layers. For example, highly efficient cathodes such as Ca, Ba or LiF may be used. Shaped substrates and novel hole-transporting materials which bring about a reduction in the operating voltage or an increase in the quantum efficiency are likewise usable in the inventive OLEDs. Furthermore, additional layers may be present in the OLEDs in order to adjust the energy level of the different layers and to facilitate electroluminescence.

The inventive OLEDs may be used in all devices in which electroluminescence is useful. Suitable devices are preferably selected from stationary and mobile visual display units. Stationary visual display units are, for example, visual display units of computers, televisions, visual display units in printers, kitchen appliances and advertising panels, illuminations and information panels. Mobile visual display units are, for example, visual display units in cellphones, laptops, cameras, especially digital cameras, vehicles and destination displays on buses and trains.

In addition, the cyclic phosphazene compounds of the formula (I) or (II) may be used in OLEDs with inverse structure. The structure of inverse OLEDs and the materials customarily used therein are known to those skilled in the art.

The examples which follow provide additional illustration of the invention:

EXAMPLES

I. Preparation of Cyclic Phosphazene Compounds of the General Formula I

I.1 Instruments and Chemicals Used

I.1.1 Instruments $^1$H, $^{13}$C, $^{31}$P NMR spectroscopy BRUKER AC 250 (250 MHz)

Mass spectrometry Finnigan Mat 8500, MAT 112 S Varian with EI ionization

Oligomer GPC Waters model 510 with
  UV detector (WATERS 486, 254 nm)
  RI detector (WATERS 410)
  Columns: PL-Gel (pore size 100, 500 Å; particle size: 5 μm, length: 60 cm)
  Eluent: THF, calibration with polystyrene standards
  Flow rate: 0.5 mL/min Fluorescence spectroscopy SHIMADZU RF-5301 PC spectrofluorometer UV/VIS spectroscopy HITACHI U-3000 spectrophotometer Spin-coater B 0574, HAMATECH GmbH
  HS 485 Processcontrol, HAMATECH GmbH Thermogravimetry NETSCH simultaneous thermoanalysis, STR 409 C; heating rate: 10 K/min DSC Diamond DSC Flash chromatography silica gel, 0.04-0.063 mm, Merck Thin-layer chromatography Polygram SIL G/UV$_{254}$ thin-layer plates, Roth Profilometer Sloan Dektak 3030ST. Rev. 5.2/5.1/F5.0

Vapor deposition system PLS 500, Balzers

Electroluminescence detector MINOLTA LS-100 luminance meter

OLED characterization Grundig Electronics PN300, KEITHLEY model 2000 multimeter

I.1.2 Solvents and Chemicals Used

All commercial chemicals are used without further purification after receipt. All solvents for reaction and purification are distilled once before use; tetrahydrofuran (THF) was additionally distilled over potassium.

I.2 Synthesis Methods and Characterization of the Compounds

I.2.1 Bis(3,5-dimethylphenyl)phosphinic acid

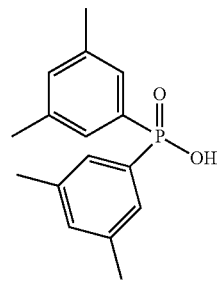 [SMILES: Cc1cc(C)cc(P(=O)(O)c2cc(C)cc(C)c2)c1]

1-Bromo-3,5-dimethylbenzene (13.63 g, 71.44 mmol, 97%) is added dropwise at room temperature to magnesium turnings (1.74 g, 71.44 mmol) in anhydrous THF (80 mL). Once the magnesium has dissolved completely, a solution of N,N-dimethylphosphoryl dichloride N(Me)$_2$P(O)Cl$_2$ (4.33 mL, 35.72 mmol) in anhydrous THF (10 mL) is added dropwise. To remove the salt formed in the reaction, the reaction mixture, after two hours, is added to an ice-cooled ammonium chloride solution (30 g in 500 mL of water). In a distillation apparatus, the THF is subsequently removed and the residue is boiled with concentrated HCl (75 mL) at 80° C. The resulting white solid is dissolved in aqueous NaOH (5.4 g, 300 mL of water) and the aqueous phase is extracted twice with diethyl ether. The clear aqueous phase is acidified again by adding concentrated HCl, in order to precipitate the phosphinic acid as a white solid in 70% yield (6.81 g).

Characterization:
$^1$H NMR (CDCl$_3$) δ(ppm): 11.35 (s, 1H, OH), 7.35 (d, 4H, o-Hs), 7.11 (s, 2H, p-Hs), 2.28 (m, 12H, CH$_3$).
MS m/z (%): 274 (M$^+$, 100), 259 (M-CH$_3$$^+$, 39), 136 (M$^{2+}$, 5).

I.2.2 Bis(4-methoxyphenyl)phosphinic acid

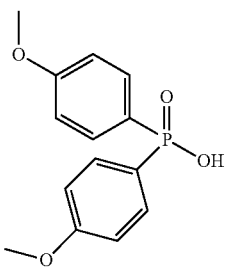 [SMILES: COc1ccc(P(=O)(O)c2ccc(OC)cc2)cc1]

The synthesis is effected analogously to the above-described synthesis of bis(3,5-dimethylphenyl)phosphinic acid.

| 9.03 mL (71.44 mmol) of | 4-bromoanisole, 99% |
| 1.74 g (71.44 mmol) of | magnesium |
| 4.33 mL (35.72 mmol) of | N,N-dimethylphosphoryl dichloride 98% |
| 80 mL of | THF (abs.) |

Yield: 54% (5.36 g) of white solid.

Characterization:
$^1$H NMR (CDCl$_3$) δ(ppm): 7.77 (br s, 1H, OH), 7.62 (dd, 4H, meta-Hs), 6.83 (dd, 4H, ortho-Hs), 3.79 (m, 6H, methoxy).
MS m/z (%): 278 (M$^+$, 100), 263 (M-CH$_3$$^+$, 19), 247 (M-OCH$_3$, 8), 107 (M-(C$_6$H$_4$—OCH$_3$, 15).

I.2.3 Bis(3,5-dimethylphenyl)phosphinamide

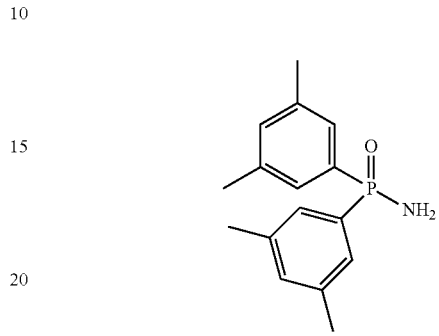

Distilled thionyl chloride (0.87 mL, 12 mmol) is added dropwise to a suspension of bis(3,5-dimethylphenyl)phosphinic acid (1 g, 3.65 mmol) in dry toluene (25 mL) at 55-60° C. and the resulting clear solution is stirred for 20 min. After the excess thionyl chloride has been distilled off, ammonia gas is introduced into the solution at −20° C. In order to remove the salt formed (NH$_4$Cl), the organic phase is washed with water. Before the extraction with THF, the density of the aqueous phase is increased by adding sodium chloride. After the organic phase has been dried over Na$_2$SO$_4$, the solvent is removed on a rotary evaporator. The yield is 0.98 g (98%).

Characterization:
$^1$H NMR (CDCl$_3$) δ(ppm): 7.53 (d, 4H, o-Hs), 7.11 (s, 2H, p-Hs), 3.01 (br s, 2H, NH$_2$), 2.32 (m, 12H, CH$_3$).
MS m/z (%): 273 (M$^+$, 100), 257 (M-NH$_2$$^+$, 19).

I.2.4 Bis(3,5-dimethylphenyl)phosphinamide

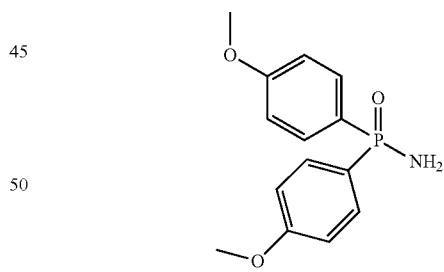

The synthesis is effected analogously to the above-described synthesis of bis(3,5-dimethylphenyl)phosphinamide.

| 1.0 g (3.59 mmol) | bis(4-methoxyphenyl)phosphinic acid |
| 0.78 ml (10.77 mmol) | thionyl chloride |
| 25 mL | dry toluene |

Yield: 90% (0.89 g) of yellowish solid.

Characterization:
$^1$H NMR (CDCl$_3$) δ(ppm): 7.83 (dd or m, 4H, meta-Hs), 6.92 (dd or m, 4H, ortho-Hs), 3.81 (m, 3H, methoxy), 3.08 (br s, 1.7Hs, NH$_2$).

MS m/z (%): 277 (M$^+$, 100), 170 (M-(methoxyphenyl)$^+$, 45).

I.2.5 Hexaphenylcyclotriphosphazene (1a)

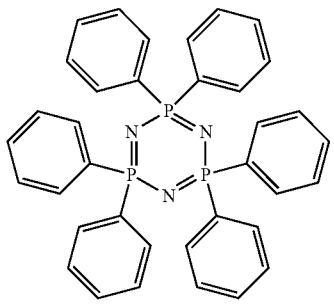 [SMILES: c1ccc(P2(c3ccccc3)=NP(c3ccccc3)(c3ccccc3)=NP(c3ccccc3)(c3ccccc3)=N2)cc1]

A suspension composed of diphenylphosphinamide (2.0 g, 9.22 mmol), triphenylphosphine (2.9 g, 11.1 mmol), carbon tetrachloride (0.89 mL, 9.22 mmol) and triethylamine (1.3 mL, 9.22 mmol) in dry dichloromethane (25 mL) is boiled under reflux for five hours. The solvent is removed on a rotary evaporator. After column chromatography with hexane:THF (1:1) as the eluent, 1.2 g (65%) of hexaphenylcyclotriphosphazene are obtained as a white substance. Further purification is effected by means of sublimation.

Characterization:

$^1$H NMR (CDCl$_3$) δ(ppm): 7.76 (dd, 12H, ortho-Hs), 7.30 (m, 18H, meta-/para-Hs).

$^{13}$C NMR (CDCl$_3$) δ(ppm): 138.55 (dt, C$_{P\text{-}bound}$), 130.86 (ps d, C$_{meta}$), 130.44 (m, C$_{para}$), 127.98 (ps d, C$_{ortho}$).

$^{31}$P NMR (CDCl$_3$) δ(ppm): 16.24

Elemental analysis Calculated: C, 72.36%, H, 5.06%, N: 7.03%, P: 15.55%

Found: C, 72.38%, H, 5.08%, N: 7.07%, P: 15.49%

MS m/z (%): 597 (M$^+$, 100), 520 (M-Ph$^+$, 74), 299 (M$^{2+}$, 12), 260 (M$^{2+}$-Ph, 18), 77 (Ph$^+$, 5).

I.2.6 Hexa(3,5-dimethylphenyl)cyclotriphosphazene (1b)

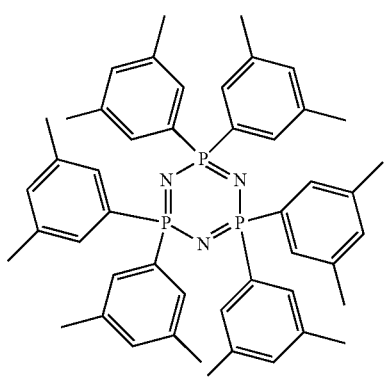

The synthesis is effected analogously to the above-described synthesis of hexaphenylcyclotriphosphazene. The reaction time is 22 hours.

| 1.0 g (3.66 mmol) | bis(3,5-dimethylphenyl)phosphinamide |
| 1.15 g (4.39 mmol) | triphenylphosphine |
| 0.53 mL (5.49 mmol) | carbon tetrachloride |
| 0.76 mL (5.49 mmol) | triethylamine |
| 25 mL | dry dichloromethane |

Column chromatography with hexane:THF (10:1) as the eluent affords 660 mg (71%) of hexa(3,5-dimethylphenyl)cyclotriphosphazene as a white solid. Further purification is effected by means of sublimation.

Characterization:

$^1$H NMR (CDCl$_3$) δ(ppm): 7.40 (d, 12H, ortho-Hs), 6.98 (s, 6H, para-Hs), 2.21 (m, 36H, CH$_3$).

$^{13}$C NMR (CDCl$_3$) δ(ppm): 138.35 (dt, C$_{P\text{-}bound}$), 137.16 (ps d, C$_{meta}$), 131.97 (d, C$_{para}$), 128.90 (d, C$_{ortho}$), 21.34 (s, methyl).

Elemental analysis Calculated: C, 75.27%, H, 7.11%, N: 5.49%, P: 12.13%

Found: C, 75.14%, H, 7.04%, N: 5.54%, P: 12.18%

MS m/z (%): 765 (M$^+$, 100), 660 (M-Ph$^+$, 45), 382 (M$^{2+}$, 10), 105 (meta-xylene$^+$, 10).

I.2.7 Hexa(4-methoxyphenyl)cyclotriphosphazene (1c)

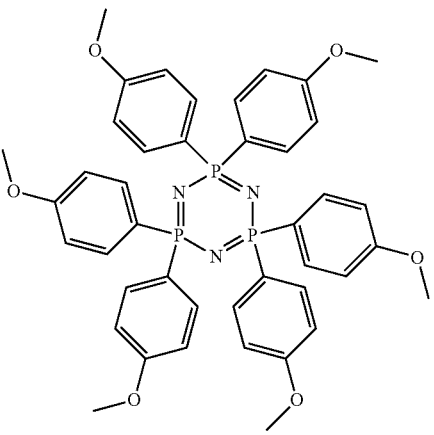

The synthesis is effected analogously to the above-described synthesis of hexaphenylcyclotriphosphazene. The reaction time is 14 hours.

| 1.11 g (4 mmol) | bis(4-methoxyphenyl)phosphinamide |
| 1.26 g (4.8 mmol) | triphenylphosphine |
| 0.58 mL (6 mmol) | carbon tetrachloride |
| 0.83 mL (6 mmol) | triethylamine |
| 35 mL | dry dichloromethane |

Column chromatography with hexane:ethyl acetate (1:1) as the eluent affords 516 mg (50%) of hexa(4-methoxyphenyl)cyclotriphosphazene as a white solid.

Characterization:

$^1$H NMR (CDCl$_3$) δ(ppm): 7.64 (dd or m, 12H, meta-Hs), 6.80 (dd or m, 12H, ortho-Hs), 3.78 (m, 18H, methoxy).

$^{13}$C NMR (CDCl$_3$) δ(ppm): 161.24 (m, C$_{para}$), 132.71 (ps d, C$_{meta}$), 130.84 (dt, C$_{P\text{-}bound}$), 113.39 (ps d, C$_{ortho}$), 55.31 (s, methoxy).

Elemental analysis Calculated: C, 64.86%, H, 5.44%, N: 5.40%, O: 12.34%, P: 11.95%

Found: C, 65.28%, H, 5.44%, N: 5.76%, O: 12.69%, P: 10.81%

MS m/z (%): 777 (M$^+$, 99), 670 (M-(methoxyphenyl))$^+$, 45), 388 (M$^{2+}$, 22).

II OLED Comprising hexaphenylcyclotriphosphazene (1a) as Matrix Material

II.1 Diode Construction

The diode construction used is the layer sequence shown in FIG. 1.

In FIG. 1:

BAlq (40 nm) is a 40 nm-thick hole-blocking electron conductor layer of aluminum(III)bis(2-methyl-8-quinolinate)-4-phenylphenoxide (A)

1a: Flrpic is an emission layer of 15% by weight of Flrpic (B) in 1a as matrix (layer thicknesses of 20 and 26 nm as mentioned below)

CBP (15 nm) is a 15 nm-thick layer of 4,4'-bis(carbazol-9-yl)biphenyl (C)

NPD (40 nm) is a 40 nm-thick hole transport layer of N,N'-diphenyl-N,N'-bis(1-naphthyl)-1,1'-biphenyl-4,4"-diamine (D)

ITO (80 nm) is an 80 nm-thick layer of indium tin oxide

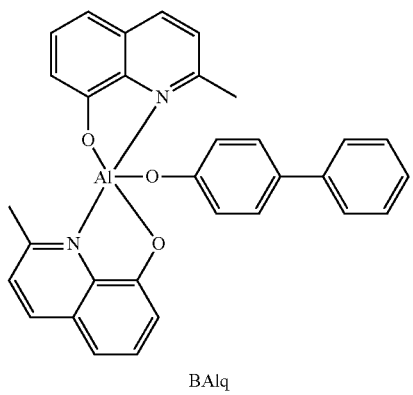

BAlq (A)

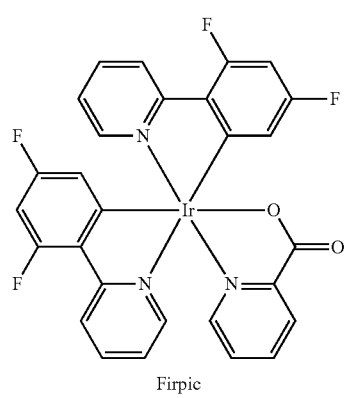

Flrpic (B)

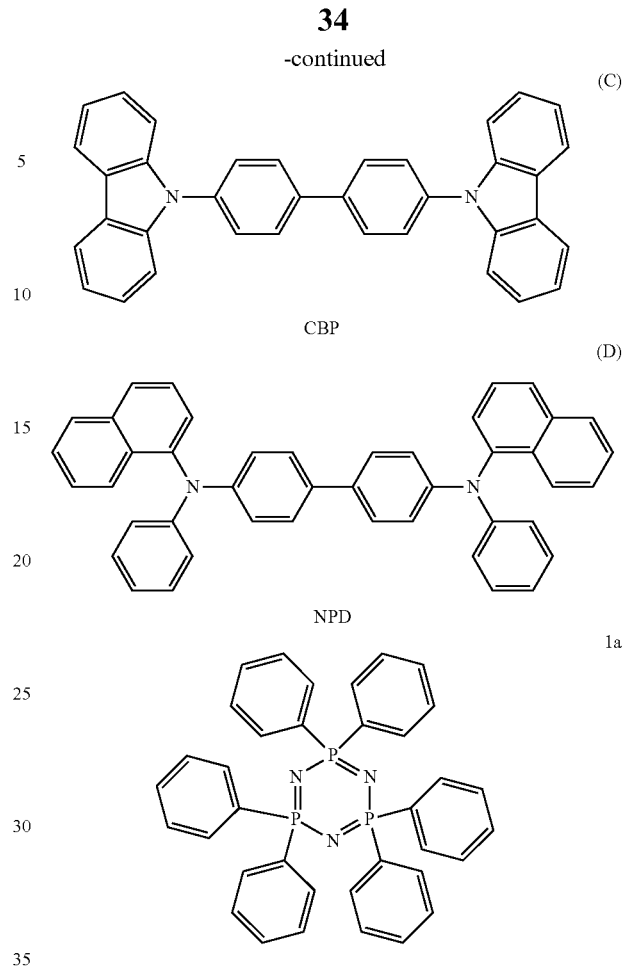

CBP (C)

NPD (D)

1a

II.2 Production of the OLED 40 nm of NPD are applied by vapor deposition to an ITO substrate as hole transport material. The subsequent 15 nm-thick CBP layer functions here as an energetic level between the HOMO levels of NPD and 1a, which is intended to facilitate hole transport into the emission layer. In a combinatorial experiment, different layer thicknesses (20 nm, 26 nm) for the emission layer are applied by vapor deposition, said layer consisting of 15% Flrpic in 1a as a matrix. A 40 nm-thick BAlq layer constitutes the hole-blocking electron conductor layer. Finally, 1 nm of lithium fluoride and 200 nm of aluminum are applied as electrode material.

Figure 2A:
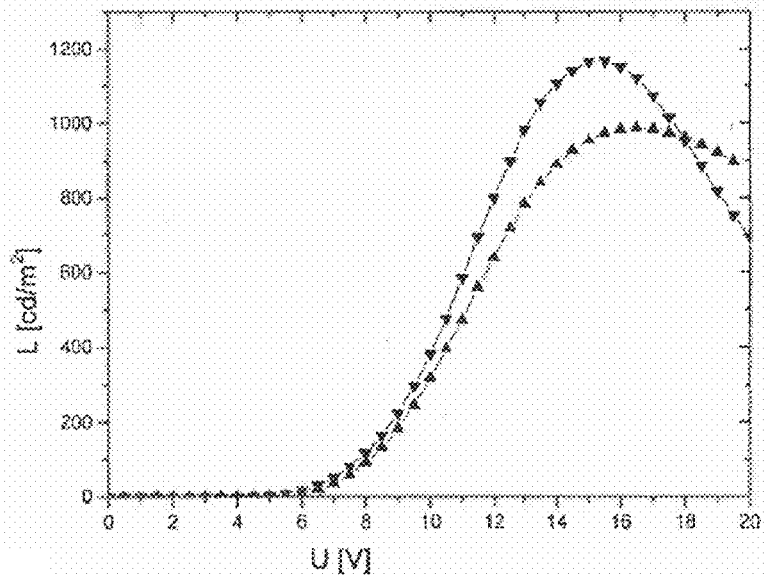
FIG. 2a shows curves of luminance as a function of voltage.
Figure 2B:
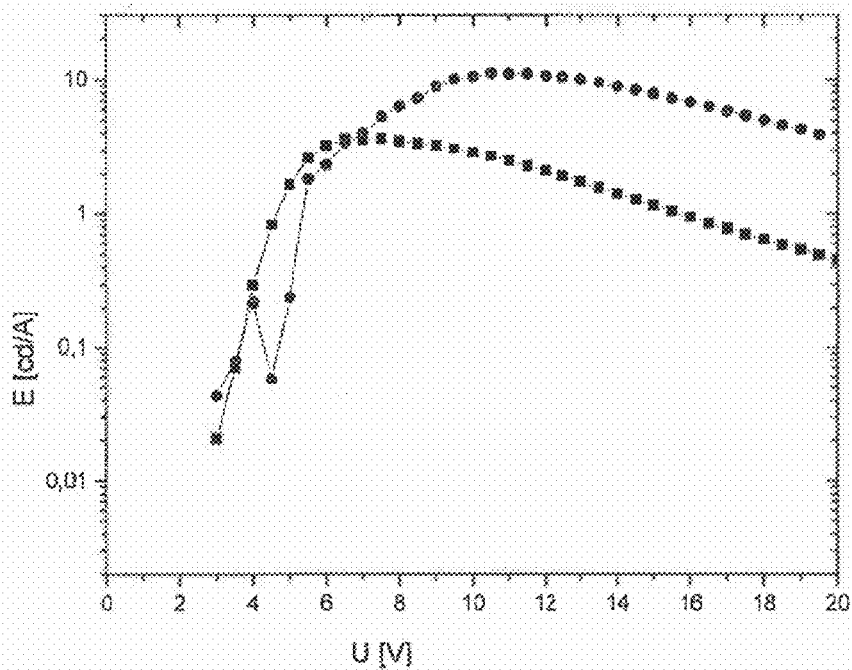
FIG. 2b shows curves of efficiency as a function of voltage.

The luminance and the efficiency of the OLED are shown in FIG. 2a and FIG. 2b for layer thicknesses of the emission layer of 20 nm and 26 nm.

In FIG. 2a:

L [cd/m$^2$] means luminance in cd/m$^2$

U [V] means voltage applied in V

The curve with the reversed triangles (tip downward) indicates the data for a 20 nm-thick emission layer and the curve with the triangles (tip upward) indicates the data for a 26 nm-thick emission layer.

In FIG. 2b:

E [cd/A] means efficiency in cd/A

U [V] means voltage applied in V

The curve with the squares indicates the data for a 20 nm-thick emission layer and the curve with the circles indicates the data for a 26 nm-thick emission layer.

II.3 Result

The OLED with a 20 nm-thick emission layer exhibits a somewhat higher luminance of 1200 cd/m$^2$ (15 V, 100 mA/cm$^2$) compared to 980 cd/m$^2$ (15 V, 12 mA/cm$^2$) in the case of the 26 nm-thick emission layer. In the case of the 26 nm-thick emission layer, an efficiency maximum of 11.0 cd/A at 10.5 V and a luminance of 500 cd/m$^2$ are achieved. The highest efficiency of 3.6 cd/A occurs at 7.5 V and a luminance of only 50 cd/m$^2$ for the 20 nm-thick emission layer.

The invention claimed is:

1. An organic light-emitting diode, comprising at least one cyclic phosphazene compound of formula (I)

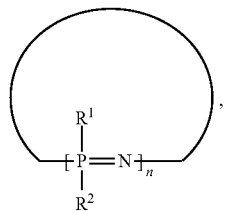

wherein:
n is from 3 to 8;
$R^1$ and $R^2$ are each the same or different, and each independently a substituted or unsubstituted aryl, a substituted or unsubstituted heteroaryl, a substituted or unsubstituted alkyl, a substituted or unsubstituted aryloxy, a substituted or unsubstituted alkyloxy, an unsubstituted or substituted cycloalkyl, an unsubstituted or substituted heterocycloalkyl, an unsubstituted or substituted alkenyl, an unsubstituted or substituted alkynyl, an unsubstituted or substituted aralkyl, or F;
or
$R^1$ and $R^2$ are each independently, in the n groups of formula (I), joined to one another via a bond, a $C_1$-$C_6$-alkylene bridge, an arylene bridge, or a $C_2$-$C_6$-alkenylene bridge, such that $R^1$ and $R^2$ together with the phosphorus atom to which they are joined form a cycle;
wherein at least one of $R^1$ and $R^2$ is joined to at least one of the phosphorus atoms of the at least one cyclic phosphazene compound of formula (I) not via an oxygen atom, and
wherein the at least one cyclic phosphazene compound is a matrix material in a light-emitting layer, a hole/exciton blocker material, an electron conductor, an electron injection material, an electron/exciton blocker material, a hole injection material and/or a hole conductor.

2. The organic light-emitting diode according to claim 1, wherein, in the at least one cyclic phosphazene compound, the at least one $R^1$ or $R^2$ joined to the at least one of the phosphorus atoms of the at least one cyclic phosphazene compound of the formula (I), is joined via a carbon atom.

3. The organic light-emitting diode according to claim 1, wherein, in the at least one cyclic phosphazene compound, n is 3.

4. The organic light-emitting diode according to claim 1, wherein, in the at least one cyclic phosphazene compound, the at least one $R^1$ or $R^2$ joined to the at least one of the phosphorus atoms of the at least one cyclic phosphazene compound of formula (I) not via an oxygen atom, is an unsubstituted or substituted aryl radical or an unsubstituted or substituted heteroaryl radical.

5. The organic light-emitting diode according to claim 1, wherein, in the at least one cyclic phosphazene compound, $R^1$ and $R^2$ are each the same or different, and are each independently substituted or unsubstituted aryl or substituted or unsubstituted heteroaryl.

6. The organic light-emitting diode according to claim 2, wherein the at least one cyclic phosphazene compound has formula (Ia)

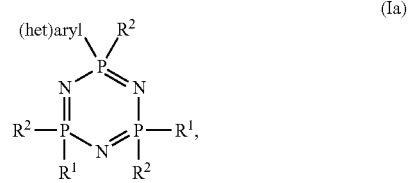

wherein:
(het)aryl is an unsubstituted or substituted $C_{6-14}$-aryl, or an unsubstituted or substituted heteroaryl which has from 5 to 14 ring atoms and is joined to the P of the phosphazene ring via a carbon atom;
$R^1$ and $R^2$ are each the same or different, and are each independently a substituted or unsubstituted aryl, a substituted or unsubstituted heteroaryl, a substituted or unsubstituted alkyl, a substituted or unsubstituted aryloxy, or a substituted or unsubstituted alkyloxy;
Or
$R^1$ and $R^2$ are each independently joined to one another via a bond, a $C_1$-$C_6$-alkylene bridge, an arylene bridge, or a $C_2$-$C_6$-alkenylene bridge, such that $R^1$ and $R^2$ together with the phosphorus atom to which they are joined form a cycle.

7. The organic light-emitting diode according to claim 6, wherein all $R^1$, $R^2$, and (het)aryl radicals in the at least one cyclic phosphazene compound of formula (Ia) are identical.

8. The organic light-emitting diode according to claim 1, wherein the at least one cyclic phosphazene compound is a matrix material in the light-emitting layer and/or a hole/exciton blocker material and/or an electron conductor.

9. The organic light-emitting diode according to claim 1, having an emission maximum between 400 and 500 nm.

10. The organic light-emitting diode according to claim 1, comprising a light-emitting layer comprising at least one matrix material and at least one emitter material, wherein the at least one matrix material comprises the at least one cyclic phosphazene compound according to claim 1.

11. A device selected from the group consisting of a stationary visual display unit, an illumination, and a mobile visual display unit, comprising at least one organic light-emitting diode according to claim 1.

12. The organic light emitting diode according to claim 6, wherein in wherein the at least one cyclic phosphazene compound of formula (Ia),
$R^1$ and $R^2$, in the case where they are joined to one another, together independently, in the n groups of formula (I), form one of:

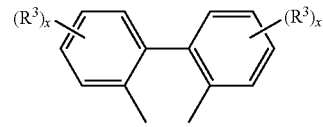

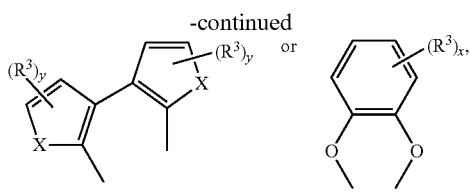

wherein:
R³ is, in each case, independently a substituted or unsubstituted aryl, a substituted or unsubstituted heteroaryl, a substituted or unsubstituted alkyl, a substituted or unsubstituted aryloxy, a substituted or unsubstituted alkyloxy, an unsubstituted or substituted cycloalkyl, an unsubstituted or substituted heterocycloalkyl, an unsubstituted or substituted alkenyl, an unsubstituted or substituted alkynyl, am unsubstituted or substituted aralkyl or halogen, or pseudohalogen;
X is a heteroatom;
x is, in each case, independently 0, 1, 2, 3, or 4; and
y is, in each case, each independently 0, 1, or 2.

13. The organic light-emitting diode according to claim 1, wherein, in the at least one cyclic phosphazene compound, R¹ or R² are the same or different, and are each independently a substituted or unsubstituted aryl, a substituted or unsubstituted heteroaryl, a substituted or unsubstituted alkyl, a substituted or unsubstituted aryloxy, or a substituted or unsubstituted alkyloxy.

14. The organic light-emitting diode according to claim 1, wherein, in the at least one cyclic phosphazene compound, n is 3 or 4.

15. The organic light-emitting diode according to claim 6, wherein, in the at least one cyclic phosphazene compound of formula (Ia),
(het)aryl is phenyl, a $C_1$-$C_6$-alkylphenyl, a $C_1$-$C_6$-dialkylphenyl, a $C_1$-$C_6$-alkoxyphenyl or a $C_1$-$C_6$-dialkoxyphenyl.

16. The organic light-emitting diode according to claim 6, wherein, in the at least one cyclic phosphazene compound of formula (Ia),
(het)aryl is an unsubstituted or substituted carbazolyl, an unsubstituted or substituted azacarbazolyl, or an unsubstituted or substituted pyridyl.

* * * * *